United States Patent
Steele et al.

(10) Patent No.: US 7,634,365 B2
(45) Date of Patent: *Dec. 15, 2009

(54) INSPECTION SYSTEM AND APPARATUS

(75) Inventors: M. Brandon Steele, Decatur, GA (US); Jeffrey Alan Hawthorne, Decatur, GA (US)

(73) Assignee: Qcept Technologies, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/036,897

(22) Filed: Feb. 25, 2008

(65) Prior Publication Data

US 2008/0162066 A1 Jul. 3, 2008

Related U.S. Application Data

(63) Continuation of application No. 11/519,501, filed on Sep. 12, 2006, now Pat. No. 7,337,076, which is a continuation of application No. 11/078,255, filed on Mar. 11, 2005, now Pat. No. 7,107,158, which is a continuation-in-part of application No. 10/710,836, filed on Aug. 5, 2004, now Pat. No. 7,103,482, which is a continuation-in-part of application No. 10/771,628, filed on Feb. 3, 2004, now Pat. No. 7,308,367, which is a continuation-in-part of application No. 10/631,469, filed on Jul. 29, 2003, now Pat. No. 6,957,154.

(60) Provisional application No. 60/444,504, filed on Feb. 3, 2003.

(51) Int. Cl.
*G01B 5/28* (2006.01)

(52) U.S. Cl. ...................................................... 702/35

(58) Field of Classification Search ................... 702/35, 702/39, 81, 167, 168, 171; 700/109, 110, 700/121
See application file for complete search history.

(56) References Cited

U.S. PATENT DOCUMENTS 4,166,974 A 9/1979 Vermeers (Continued)

FOREIGN PATENT DOCUMENTS

DE 297509 A5 1/1992

(Continued)

OTHER PUBLICATIONS

Yang Y et al: "Kelvin probe study on the perfluoropolyether film on metals", Tribology Letters, 2001, Kluwer Academic/Plenum Publishers, USA, vol. 10, No. 4, pp. 211-216, XP009035197, ISSN: 1023-8883 (p. 211-p. 212).

(Continued)

*Primary Examiner*—Michael P. Nghiem
*Assistant Examiner*—Cindy H Khuu
(74) *Attorney, Agent, or Firm*—Foley & Lardner LLP

(57) ABSTRACT

A method and system for identifying a defect or contamination on a surface of a sample. The system operates by detecting changes in work function across a surface via both vCPD and nvCPD. It utilizes a non-vibrating contact potential difference (nvCPD) sensor for imaging work function variations over an entire sample. The data is differential in that it represents changes in the work function (or geometry or surface voltage) across the surface of a sample. A vCPD probe is used to determine absolute CPD data for specific points on the surface of the sample. The combination of vibrating and non-vibrating CPD measurement modes allows the rapid imaging of whole-sample uniformity, and the ability to detect the absolute work function at one or more points.

33 Claims, 34 Drawing Sheets

U.S. PATENT DOCUMENTS

| | | | |
|---|---|---|---|
| 4,295,092 A | 10/1981 | Okamura | |
| 4,481,616 A | 11/1984 | Matey | |
| 4,973,910 A | 11/1990 | Wilson | |
| 5,087,533 A | 2/1992 | Brown | |
| 5,136,247 A | 8/1992 | Hansen | |
| 5,214,389 A | 5/1993 | Cao et al. | |
| 5,217,907 A | 6/1993 | Bulucea et al. | |
| 5,218,362 A | 6/1993 | Mayes et al. | |
| 5,270,664 A | 12/1993 | McMurtry et al. | |
| 5,272,443 A | 12/1993 | Winchip et al. | |
| 5,278,407 A | 1/1994 | Ikebe et al. | |
| 5,293,131 A | 3/1994 | Semones et al. | |
| 5,315,259 A | 5/1994 | Jostlein | |
| 5,369,370 A | 11/1994 | Stratmann et al. | |
| 5,381,101 A | 1/1995 | Bloom et al. | |
| 5,460,684 A | 10/1995 | Saeki et al. | |
| 5,517,123 A | 5/1996 | Zhao et al. | |
| 5,546,477 A | 8/1996 | Knowles et al. | |
| 5,583,443 A | 12/1996 | McMurtry et al. | |
| 5,723,980 A | 3/1998 | Haase et al. | |
| 5,723,981 A | 3/1998 | Hellemans et al. | |
| 5,773,989 A | 6/1998 | Edelman et al. | |
| 5,974,869 A | 11/1999 | Danyluk et al. | |
| 5,977,788 A | 11/1999 | Lagowski | |
| 6,011,404 A | 1/2000 | Ma et al. | |
| 6,037,797 A | 3/2000 | Lagowski et al. | |
| 6,091,248 A | 7/2000 | Hellemans et al. | |
| 6,094,971 A | 8/2000 | Edwards et al. | |
| 6,097,196 A | 8/2000 | Verkuil et al. | |
| 6,114,865 A | 9/2000 | Lagowski et al. | |
| 6,127,289 A | 10/2000 | Debusk | |
| 6,139,759 A | 10/2000 | Doezema et al. | |
| 6,198,300 B1 | 3/2001 | Doezema et al. | |
| 6,201,401 B1 | 3/2001 | Hellemans et al. | |
| 6,232,134 B1 | 5/2001 | Farber et al. | |
| 6,255,128 B1 | 7/2001 | Chacon et al. | |
| 6,265,890 B1 | 7/2001 | Chacon et al. | |
| 6,517,669 B2 | 2/2003 | Chapman | |
| 6,520,839 B1 | 2/2003 | Gonzalez-Martin et al. | |
| 6,538,462 B1 | 3/2003 | Lagowski et al. | |
| 6,546,814 B1 | 4/2003 | Cloe et al. | |
| 6,551,972 B1 | 4/2003 | Lei et al. | |
| 6,597,193 B2 | 7/2003 | Lagowski et al. | |
| 6,664,546 B1 | 12/2003 | McCord et al. | |
| 6,664,800 B2 | 12/2003 | Chacon et al. | |
| 6,679,117 B2 | 1/2004 | Danyluk et al. | |
| 6,680,621 B2 | 1/2004 | Savtchouk et al. | |
| 6,711,952 B2 | 3/2004 | Leamy et al. | |
| 6,717,413 B1* | 4/2004 | Danyluk et al. | 324/459 |
| 6,771,091 B2* | 8/2004 | Lagowski et al. | 324/765 |
| 6,776,030 B1* | 8/2004 | Kirpichnikov et al. | 73/105 |
| 6,791,310 B2 | 9/2004 | Smith | |
| 6,803,241 B2 | 10/2004 | Eom et al. | |
| 6,849,505 B2 | 2/2005 | Lee et al. | |
| 6,957,154 B2* | 10/2005 | Steele et al. | 702/35 |
| 7,019,654 B2 | 3/2006 | Danyluk et al. | |
| 7,103,482 B2* | 9/2006 | Steele et al. | 702/35 |
| 7,107,158 B2* | 9/2006 | Steele et al. | 702/35 |
| RE39,803 E * | 9/2007 | Danyluk et al. | 73/105 |
| 7,308,367 B2* | 12/2007 | Steele et al. | 702/35 |
| 7,337,076 B2* | 2/2008 | Steele et al. | 702/35 |
| 2003/0139838 A1 | 7/2003 | Marcella | |
| 2003/0164942 A1 | 9/2003 | Take | |
| 2003/0175945 A1 | 9/2003 | Thompson et al. | |
| 2004/0029131 A1 | 2/2004 | Thompson et al. | |
| 2004/0057497 A1 | 3/2004 | Lagowski et al. | |
| 2004/0058620 A1 | 3/2004 | Gotkis et al. | |
| 2004/0105093 A1 | 6/2004 | Hamamatsu et al. | |
| 2004/0134515 A1 | 7/2004 | Castrucci | |
| 2005/0016279 A1* | 1/2005 | Hawthorne et al. | 73/593 |
| 2009/0139312 A1* | 6/2009 | Hawthorne et al. | 73/105 |

FOREIGN PATENT DOCUMENTS

| | | |
|---|---|---|
| EP | 1039277 | 3/2000 |
| EP | 1304463 | 4/2003 |
| WO | WO 01/90730 A2 | 11/2001 |
| WO | WO 2004/070355 A2 | 8/2004 |

OTHER PUBLICATIONS

Yano D et al: "Nonvibrating contact potential difference probe measurement of a nanometer-scale lubricant on a hard disk", Journal of Tribology, American Society of Mechanical Engineers, New York, NY, US; vol. 121, No. 4, Oct. 1999, pp. 980-983, XP008031092, ISSN: 0742-4787 (pp. 980-981, fig. 4, first ref. on p. 983).

Castaldini A et al: "Surface analyses of polycrystalline and Cz-Si wafers", Solar Energy Materials and Solar Cells, Elsevier Science Publishers, Amsterdam, NL; vol. 72, No. 1-4, Apr. 2002, pp. 425-432, XP004339790, ISSN: 0927-0248 (whole document).

Korach C S et al: "Measurement of perfluoropolyether lubricant thickness on a magnetic disk surface", Applied Physics Letters, American Institute of Physics, New York, NY, US; vol. 79, No. 5, Jul. 30, 2001, pp. 698-700, XP012029958, ISSN: 0003-6951 (p. 699, left column; fig. 2).

Yang Y et al: "Kelvin probe study on the perfluoropolyether film on metals", Tribology Letters, 2001, Kluwer Academic/Plenum Publishers, USA, vol. 10, No. 4, pp. 211-216, XP009035197, ISSN: 1023-8883 (p. 211-p. 212).

Castaldini A et al: "Scanning Kelvin probe and surface photovoltage analysis of multicrystalline silicon", Materials Science and Engineering B., Elsevier Sequoia, Lausanne, CH; vol. 91-92, Apr. 30, 2002, pp. 234-238, XP004355534, ISSN: 0921-5107 (chapters "2.2 Scanning Kelvin probe: and 4.2 Scanning Kelvin probe analyses").

Lagel B et al: "A novel detection system for defects and chemical contamination in semiconductors based upon the scanning Kelvin probe", 14th International Vacuum Congress (IVC-14). 10th International Conference on Solid Surfaces (ICS-10). 5th International Conference on Nanometre-Scale Science and Technology (NANO-5). 10th International Conference on Quantitative Surface Analysis; vol. 433-435, pp. 622-626, XP002292441, Surface Science, Aug. 2, 1999, Elsevier, NL, ISSN: 003906028 (whole document).

Ren J et al: "Scanning Kelvin Microscope: a new method for surface investigations" 8. Arbeitstatgung Angewandte Oberflachenanalytik 'AOFA 8' ('Applied Surface Analysis'), Kaiserslautern, DE, Sep. 5-8, 1994; vol. 353, No. 3-4, pp. 303-306, XP009035181, Fresenius' Jounal of Analytical Chemistry, Oct. 1995, Springer-Verlag, DE, ISSN: 0937-0633 (p. 304, right column; fig. 1).

Baumgartner H et al: "Micro Kelvin probe for local work-function measurements", Review of Scientific Instrumetns, May 1988, USA; vol. 59, No. 5, pp. 802-805, XP0022922442, ISSN: 0034-6748 (abstract; fig. 4, chapter "V. Results").

Danyluk S: "Non-vibrating contact potential imaging for semiconductor fabrication", Semicon West 2003, 'Online!, Jul. 14, 2003, pp. 1-15, XP002292443, retrieved from the internet: ,URL:http://dom.semi.org/web/wFiles.nsf/Lookup/TIS18_QceptTechnologiesInc/$file/TIS18%20QceptTechnologiesInc.Alternate.pdf. 'retrieved on Aug. 13, 2004 (whole document).

Moorman, M. et al., "A Novel, Micro-Contact Potential Difference Probe," Sensors and Actuators B, Elsevier Sequoia S.A., Lausanne, CH, vol. 94, No. 1.

Reid, Jr., Lennox Errol, "Surface Characterization of Hard Disks Using Non-Contact Work Function Capacitance Probe," A Thesis Presented to the Academic Faculty in Partial Fulfillment of the Requirements for the Degree of Master of Science in Mechanical Engineering, Georgia Institute of Technology, Jun. 1986.

* cited by examiner

SUBTRACTION
9-0V
BIAS

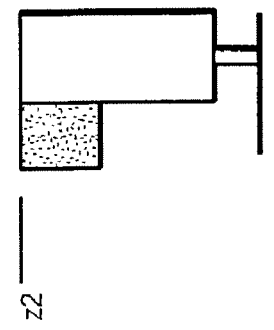
FIG. 25C
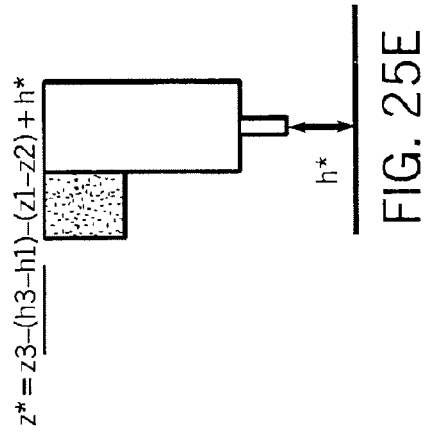
$z* = z3-(h3-h1)-(z1-z2)+h*$
FIG. 25E
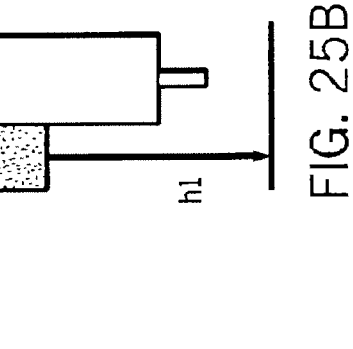
FIG. 25B
FIG. 25D
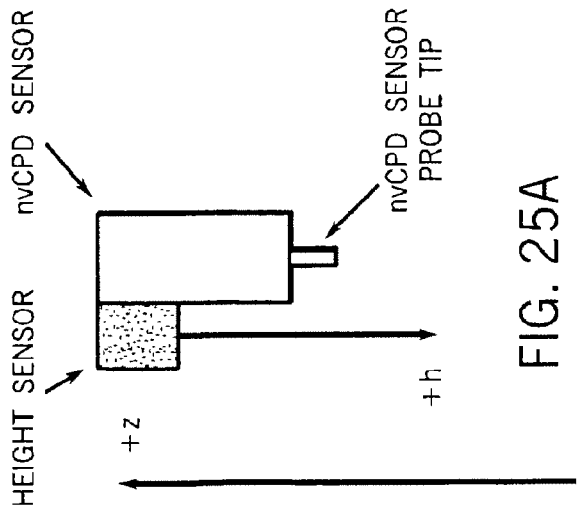
FIG. 25A

| Surface | Si | Si | Si | Au | Au | Au |
|---|---|---|---|---|---|---|
| X= | 7 mm | 7 mm | 7 mm | -7 mm | -7 mm | -7 mm |
| Y= | 0 mm | 10 mm | -10 mm | 0 mm | 10 mm | -10 mm |
| | | | | | | |
| CPD | -0.06696 | -0.1435 | -0.10084 | -0.34582 | -0.33094 | -0.36895 |
| CPD | -0.07151 | -0.13804 | -0.09782 | -0.36891 | -0.33545 | -0.36833 |
| CPD | -0.07475 | -0.13896 | -0.09694 | -0.35853 | -0.32947 | -0.35512 |
| CPD | -0.07293 | -0.12759 | -0.10207 | -0.36045 | -0.33249 | -0.35766 |
| CPD | -0.07619 | -0.13781 | -0.09217 | -0.35876 | -0.33126 | -0.36562 |
| CPD | -0.07444 | -0.13241 | -0.09897 | -0.35846 | -0.33467 | -0.35381 |
| CPD | -0.06199 | -0.12767 | -0.10051 | -0.3641 | -0.33799 | -0.35852 |
| CPD | -0.06804 | -0.13559 | -0.0981 | -0.35616 | -0.33028 | -0.35083 |
| CPD | -0.07139 | -0.13001 | -0.0901 | -0.35407 | -0.33171 | -0.3519 |
| CPD | -0.08008 | -0.1313 | -0.08941 | -0.35934 | -0.33134 | -0.35402 |
| | | | | | | |
| Mean | -0.071828 | -0.134288 | -0.096693 | -0.35846 | -0.33256 | -0.358476 |
| Std Dev | 0.005151 | 0.005315 | 0.004548 | 0.00606 | 0.00266 | 0.006775 |

INSPECTION SYSTEM AND APPARATUS

CROSS-REFERENCE TO RELATED PATENT APPLICATIONS

This application is a continuation and claims priority from U.S. patent application Ser. No. 11/519,501 (now U.S. Pat. No. 7,337,076) filed Sep. 12, 2006, which is itself a continuation of U.S. patent application Ser. No. 11/078,255 (now U.S. Pat. No. 7,107,158) filed Mar. 11, 2005, which is itself a continuation-in-part of U.S. patent application Ser. No. 10/710,836 (now U.S. Pat. No. 7,103,482) filed Aug. 5, 2004, which is itself a continuation-in-part of U.S. patent application Ser. No. 10/771,628 (now U.S. Pat. No. 7,308,367), filed Feb. 3, 2004, which is itself a continuation-in-part of U.S. patent application Ser. No. 10/631,469 (now U.S. Pat. No. 6,957,154) filed Jul. 29, 2003, which claims priority from U.S. Provisional Patent Application Ser. No. 60/444,504, filed Feb. 3, 2003.

FIELD OF THE INVENTION

The present invention is directed to methods and systems for the inspection of semiconductor wafers and other materials such as integrated circuits (IC) and any surface benefiting from inspection. Hereinafter, any material susceptible to surface inspection by the system herein described contact potential difference imaging device will be denoted generally as a "wafer". More particularly, the present invention is directed to a method and system for the characterization of microscopic and macroscopic defects through imaging and visualization of the contact potential difference topology on the wafer surface through the use of a non-vibrating contact potential difference sensor in combination with a vibrating contact potential difference sensor.

BACKGROUND OF THE INVENTION

There is a multi-billion dollar global market for semiconductor and other surface defect management which is growing both in absolute terms and as a percentage of capital equipment investment. For example, in general, there are two factors that determine the economics of a semiconductor fabrication facility at a given utilization level, namely throughput and yield. As complex new technologies such as 300 mm semiconductor wafers, copper interconnects, and reduced feature (circuit) sizes drive the margin of error in fabrication ever lower, new inspection technologies are critical to keep yields high and bottom-line economics attractive. Detection and elimination of chemical contamination and other types of defects is a constant concern for semiconductor manufacturers and equipment suppliers. Contamination can arise from use of processing chemicals, processing equipment, and poor handling techniques. Contaminants can include, for example, metals, carbon, and organic compounds. Other types of defects can result from a wide range of causes, including flaws in the semiconductor crystal, improper processing, improper handling, and defective materials. In addition, many cleaning steps are required in wafer fabrication, such as but not limited to the semiconductor industry. Each step is time consuming and requires expensive chemicals that may require special disposal procedures. Existing methods for monitoring or controlling these processes are expensive and time consuming. As a result, wafers are often cleaned for a longer period of time, using more chemicals than are required.

Continuing with the example of the semiconductor wafer industry, contamination and chemical residue are two major causes of reduced yield in semiconductor fabrication. Wafer cleanliness is becoming even more important as minimum feature sizes shrink below 90 nm, where the thickness of adsorbed layers and organic contaminants are on the same order as the process tolerances of functional films in devices. Contamination, whether organic or metallic, may generate process variation and defects such as poor coverage, vacancies, voids, leaking, shorting, and overburdens. For example, a small amount of metal contamination on the wafer surface may diffuse into the bulk semiconductor and cause the bulk minority carrier lifetime to decrease because the metal contamination may assist in the recombination of electrons and holes in the semiconductor substrate. Reducing contamination and minimizing residues are important factors in increasing yields in semiconductor wafer fabs.

Defect detection and characterization systems, such as in the semiconductor wafer industry, can usually be divided into in-line and off-line systems. "In-line" refers to inspection and measurement that takes place inside the clean room where wafers are processed. "Off-line" refers to analysis that takes place outside of the wafer processing clean room, often in a laboratory or separate clean room that is located some distance from the manufacturing area. In addition, many of these analytical techniques are destructive, which requires either the sacrifice of a production wafer or the use of expensive "monitor" wafers for analysis. In-line inspection and measurement is crucial for rapidly identifying and correcting problems that may occur periodically in these types of manufacturing processes. A typical semiconductor wafer can undergo over 500 individual process steps and require weeks to complete. Each semiconductor wafer can have a finished product value of up to $100,000. Because the number of steps and period of time involved in wafer fabrication are so large that substantial work in process can exist at any point in time. It is critical that process-related defects be found and corrected immediately before a large number (and dollar value) of wafers are affected. Such defects, regardless of the nature of the wafer, semiconductor, IC, or other device, are detrimental to performance and diminish productivity and profitability.

Many types of defects and contamination are not detectable using existing in-line tools, and these are typically detected and analyzed using expensive and time-consuming "off line" techniques (described below) such as Total Reflectance X-ray Fluorescence (TXRF), Vapor Phase Decomposition Inductively Coupled Plasma-Mass Spectrometry (VPD ICP-MS) or Secondary Ion Mass Spectrometry (SIMS). Since these techniques are used off-line (outside of the clean room used to process wafers) and usually occur hours, or even days, after the process step that has caused the contamination, their value is significantly limited.

A brief description of some well known techniques for wafer inspection and chemical contamination detection are presented in Table 1. This list is not in any sense exhaustive as there are a very large number of techniques that are used for some type of semiconductor analysis or characterization or for other surface inspection of other types of materials.

TABLE 1

| Analytical Technique | Description | In-line/Off-line |
|---|---|---|
| Total Reflection X-Ray Fluorescence (TXRF) | X-rays irradiate the wafer within the critical angle for total external reflectance, causing surface atoms to fluoresce. | Off-line |
| Automated Optical Microscopy | Optical images are acquired and automatically analyzed for detection of large defects. | In-line |
| Laser Backscattering | Wafer surface is illuminated with laser spots and the angle and/or polarization of reflected light is analyzed to detect and classify particles. | In-line |
| Vapor Phase Decomposition Inductively Coupled-Mass Spectrometry (VPD ICP-MS) | Wafers "scanned" with a drop of HF that is analyzed using mass spectrometry. | Off-line |
| Secondary Ion Mass Spectroscopy (SIMS) | Ion beam sputters the wafer surface creating secondary ions that are analyzed in a mass spectrometer. | Off-line |

Table 2 summarizes some major advantages and disadvantages of each example technique. In general, off-line detection techniques are extremely sensitive to tiny amounts of contamination; but such techniques are slow, expensive, and complex to operate. Some have limited, or no, imaging or surface mapping capability, or are destructive in nature. In-line techniques are much faster, non-destructive, and provide defect mapping, but have limited chemical contamination detection or analysis capability.

TABLE 2

| Analytical Technique | Advantages | Disadvantages |
|---|---|---|
| Total Reflection X-Ray Fluorescence (TXRF) | Very sensitive<br>Some mapping capability<br>Nondestructive | Limited coverage<br>Unpatterned wafers only |
| Automated Optical Microscopy | Fast<br>Relatively low cost<br>Detects a wide range of macro defects (>50 microns)<br>Imaging of wafer surface<br>Non-contact/non-destructive | Very limited chemical and particle detection |
| Laser Backscattering | Fast<br>Relatively low cost<br>Detects very small particles<br>Imaging of water surface<br>Non-contact/non-destructive | Only detects particles - no chemistry |
| Vapor Phase Decomposition Inductively Coupled-Mass Spectrometry (VPD ICP-MS) | Very sensitive<br>Able to identify wide range of contaminants | Destructive<br>Slow<br>Expensive<br>Complex<br>Cannot image<br>Only works on bare silicon |
| Secondary Ion Mass Spectroscopy (SIMS) | Very sensitive<br>Detects a wide range of contaminants<br>Sub-surface detection | Expensive<br>Slow<br>Destructive |

Certain types of contamination and residues can be detected with optical or analytical metrology tools. Optical inspection systems are often fast enough for in-line inspection of production wafers. However, these tools are not well suited to detecting small amounts of non-optically-visible contamination, film non-uniformities, chemical contamination, or variations in chemistry. Analytical tools, such as TXRF or TOF-SIMS, provide a wealth of information on wafer surface chemistry, but are expensive, extremely slow, destructive, or don't provide information on the whole wafer surface. Effectively detecting and controlling contamination during wafer processing requires a fast, in-line, and nondestructive method of detecting minute chemical changes on the wafer surface. The aforementioned chemical analytical methods cannot operate under such demanding in-line materials processing conditions. This capability would lead to cost savings by minimizing the time required to detect contamination, thereby reducing the number of wafers affected and the associated costs of scrap or reduced device reliability.

In general, existing in-line wafer inspection tools operate at production speeds and generate images of the wafer surface that are processed to identify and locate defects. However, these techniques are, as mentioned above, very limited in their ability to detect chemical contamination. Laser backscattering systems are limited to detecting particles down to sub-micron sizes, and optical microscopy systems can only detect chemical contamination that results in a visible stain or residue. Both techniques lack the ability to identify or classify the chemical composition of the particle or contamination. Off-line laboratory techniques are used to qualify the cleanliness of new processes and equipment, or to analyze defects detected by in-line equipment or as part of failure analysis.

Another system that has been investigated is the use of Contact Potential Difference (CPD) imaging. CPD refers to the electrical contact between two different metals and the electrical field that develops as a result of the differences in their respective maximum electronic energy level, i.e. their respective Fermi energies. When two metals are placed in contact, the Fermi energies of each will equilibrate by the flow of electrons from the metal with the lower Fermi energy to that of the higher. "Vibrating CPD sensor" refers to the vibration of one metal relative to the other in a parallel plate capacitor system. The vibration induces changes in the capacitance with time, and therefore a signal related with the surface profile. A CPD signal can also be generated by the translation of one surface past a reference sample through the use of a non-vibrating contact potential difference (nvCPD) sensor(s). This translation makes high speed scanning possible.

However, even these nvCPD sensors can themselves present certain difficulties. At a microscopic level, the surfaces of wafers are not flat due to wafer thickness variation, materials on the surface, "bowing", and other factors. In order to scan the wafer at a close but safe distance (i.e., close to the surface to promote good signal strength but far enough away to minimize any possibility of impacting the wafer surface), an appropriate sensor height must be calculated and set. Thus, the height of the sensor above the wafer surface must be measured and controlled to produce repeatable results. Furthermore, height control is also necessary to minimize the sensor height to improve resolution and signal strength. However, height is difficult to control and measure, as is the appropriate height for measurements on each specific wafer.

It is possible to use one of many commercially available height sensors to control the height of the nvCPD sensor above the wafer surface. This requires the expense of an additional sensor, and the added complexity of a calibration routine to determine the position of the nvCPD sensor tip relative to measurements made by the separate height sensor.

A related problem is the difficulty in establishing a point of reference for all distance measurements, including height, related to an nvCPD scan. A reference point is needed to produce useful measurement data for image production.

In some sensor systems, such as nvCPD sensors, it is necessary to separate the sharp peak signal from the other two components of the signal (low frequency signal and induced noise signals) to locate and measure the contaminated areas of a wafer. This is challenging because the sharp peak signal behaves like noise, i.e., it consists of sharp peaks that alternate their polarity in high frequency mode. Because of this, conventional high frequency filters based only on the frequency domain do not work, as they would degrade the sharp peak signal significantly along with the noise.

In addition, an nvCPD signal is generally delayed in time, which impacts on the quality of the nvCPD signal/image. As the sampling time increases, the time delay becomes larger. The time delay may be explained by the equivalent RC circuit modeling the electrical signal path from the probe tip to the output of the A/D converter through the amplifier, the data acquisition board and the connecting lines between them. The equivalent capacitance is mixed with the capacitance between the probe and the wafer surface, the parasitic capacitance of the connecting lines, the internal capacitance of the amplifier, and other known conventional effects. The result is that minute feature signals are less detectable, and the signal magnitude and thus the signal-to-noise ratio are smaller.

Furthermore, topographical features of a wafer often produce a weak signal in comparison to the signals from chemical features. As the usefulness of topographical versus chemical features often varies depending on the particular circumstances of an imaging application, there exists a need to be able to amplify the signal indicating topographical features or to separate, superimpose, reduce or remove signal indicating chemical features.

Also, many different types of imaging systems currently rely on a chuck to spin a sample material, such a semiconductor wafer, relative to the probe apparatus. These current designs scan the sample surface at a constant rotational speed. The probe then scans the wafer by taking circumferential tracks of data at a constant sampling rate. Due to constant rotational speed and a constant sampling rate, it is apparent that the angular separation of an individual sample will be constant over the wafer surface. However, the actual physical spacing of the data in Cartesian coordinates varies with the radius of the track being scanned. In effect the data becomes denser as the radius decreases. In addition the amount of current generated in the sensor is a linear relationship with the relative speed of the probe to sample. The actual relative speed of the sample to the probe is then related to the radius of the track of data being collected so it is not a constant when the sample is scanned at a constant rotational speed. This results in signals of larger value on the outer radius of the sample and lowers the signal towards the center of the sample which results in higher signal to noise ratio than if data density were maintained at a substantially constant level.

In addition, a need exists to increase the overall accuracy, speed, and efficiency of current inspection systems. Current systems do not meet the increasing demand from the industry to provide a method of testing a wider variety of products in a more efficient and faster manner.

In addition to a need for a system to increase the overall speed and efficiency of current inspection systems, there exists a need to provide a system which can both detect point defects, i.e. those that occur on some region of a wafer, and those whole wafer defects, i.e. those which occur uniformly across the wafer.

A need also exists for an improved scanning device which addresses the shortcomings of nvCPD sensors. Detection systems based on nvCPD systems, such as some embodiments described in the parent applications, have difficulty detecting uniform defects which occur across the entire wafer. In addition, nvCPD systems, while excellent at providing relative CPD data, are unable to determine the absolute CPD of a point on the surface. Such information is useful in both identifying material on the surface of a sample as well as in defect determination and identification.

Contamination of a whole wafer is a relatively common problem. One common defect of this type is where a chemical or elemental layer is uniformly deposited on the wafer, either where it was not intended to be or where an additional layer than was intended is applied. Conversely, wafers are produced which lack entire layers that were intended to be applied, such as where an oxide layer is not deposited as it should have been. Both of these, and particularly the last, provide distinct and difficult challenges for the inline inspection of wafers. Currently, offline, destructive techniques as described above are needed to detect this category of defect.

For example, manufacturers apply very thin (on the order of 30 nanometers) organo-silane films to wafer surfaces to function as lubrication. The minute amount of material is undetectable by optical inspection tools. The industry must utilize difficult and time-consuming tests to specifically address this issue. Thus, there exists a need to determine whether the wafer has a layer deposited thereon, and if so, to determine if the layer is of uniform thickness.

Another application where current inspection devices fail involves the removal of a thin film from a wafer or other electronic device surface. For example, it is sometimes desirable to remove a photoresist layer from a wafer. Current systems cannot efficiently determine whether the thin layer of photoresist has been removed. A need exists for a technique which can detect the presence or absence of a thin layer, while still providing information regarding surface defects.

Yet another industrial application which is in want of an improved inspection system involves the use of "witness wafers". Witness wafers are used to monitor the air quality in a semiconductor manufacturing clean room. The witness wafers are left exposed in the environment for a period of time, during which the volatile organic compounds present in the air are deposited on the wafer surface. Analytical techniques used to evaluate the witness wafer are slow and only able to spot check the wafer. An inspection method which is able to defect check the entire surface as well as to check for deposited layers of volatile organics is needed.

In the manufacturing situation, one common case of uniform contamination involves the use of a contaminated solution or deposition chamber. This may occur, for example, if the wafer is placed in a contaminated solution (for example during cleaning or plating) or in a contaminated deposition chamber (such as a Physical Vapor Deposition (PVD) or Chemical Vapor Deposition (CVD) system). In this case the contamination may be uniform across the entire wafer. Thus, processes which detect changes on the surface (e.g. nvCPD and optical) would not detect these defects.

A critical need therefore exists for a fast, inexpensive, and effective means of detecting, locating, and classifying relatively small quantities of chemical content or features and physical features on samples (and any surface which dictates ultimate performance of an electronic or chemical device), including the presence or absence of completely or nearly complete missing or additional layers on a wafer or other material. There is also a need for a system which minimizes cost and complexity of the sensor control mechanisms, such as height control. Furthermore, there is a need for methods and systems that have improved signal processing.

SUMMARY OF THE INVENTION

The present invention provides an inspection system that is a fast, inexpensive, and effective means of detecting, locating, and classifying relatively small quantities of chemical content, and physical features on materials, such as, but not limited to semiconductor wafers, integrated circuit devices, liquid crystal display panels, or any material which may benefit from such inspections, while allowing for a minimization of the complexity of the sensor control mechanisms and an improvement in signal processing.

In one embodiment, the present invention relates to an analytical method for identifying a defect present on a surface of a sample. An in-line sample processing system is provided which includes a scanning system for analyzing defects. The sample is fixed upon a sample stage of the scanning system. A positioning mechanism is provided in communication with a CPD sensor. The CPD sensor has a vibrating contact potential difference sensor mode (vCPD) and a non-vibrating contact potential difference sensor mode (nvCPD). In an nvCPD mode, the CPD difference sensor is positionable in relation to the sample stage via the positioning mechanism and the CPD sensor is positioned in the in-line sample processing system. The CPD sensor, in an nvCPD mode, continuously scans, via relative motion, the sample to generating relative CPD data. The relative CPD data is representative of relative contact potential difference along a track of the sample surface relative to the CPD sensor. The relative CPD data is assembled to form CPD data representative of the sample surface. At least one point is identified on the sample surface for measurement of absolute CPD. The CPD sensor, in a vCPD mode, is positioned above this point and absolute CPD data is generated for that point.

In another aspect, the present invention is related to a system for inline processing of a sample. The system includes a sample scanning system to identify at least one contaminant or non uniformity on a sample. A semiconductor sample stage of the scanning system is provided for receiving the sample wherein the sample stage is rotatable and engageable with the sample. The system further includes a CPD sensor system including an nvCPD probe and a vCPD probe. The CPD sensor system is in communication with a positioning assembly whereby the sensor system can be positioned relative to the sample which is secured on the sample wafer stage. The nvCPD probe is adapted to produce a relative contact potential difference signal characteristic of the contaminants on the wafer in response to a change in the CPD generated by the relative motion of the nvCPD and the sample. The vCPD probe is adapted to produce an absolute contact potential difference signal characteristic of the contaminants on the semiconductor wafer. The signal is generated by the vibration of the probe. The magnitude of the signal is related to the CPD. The vibration does not generate a change in CPD, it generates a change in capacitance between the probe and the surface. A computer system is provided in communication with the CPD sensor system, so that relative CPD data and absolute CPD data is output by the probe to the computer. This data is used to produce a visual image characteristic of the chemical contaminants and their spatial distribution on the wafer.

In yet another aspect, the present invention relates to a method for inspecting the surface of a sample wherein the contact potential difference data for substantially the entire surface of the sample is obtained using a combination of nvCPD and vCPD data. The sample surface is continuously scanned with the nvCPD mode of the CPD sensor system, generating relative CPD data from the CPD system. This relative CPD data is representative of relative CPD of the sample surface. The CPD sensor system is positioned above a point on the sample surface in vCPD mode and absolute CPD data for that point is determined. Then the absolute CPD for the sample surface is determined based on the point's absolute CPD data and the sample's relative CPD data.

BRIEF DESCRIPTION OF THE DRAWINGS

FIG. 25A illustrates an apparatus for calibration according a calibration process of the present invention for calibrating the height of the nvCPD sensor;

FIG. 25B shows the height sensor positioned above a reference surface so that the distance between the reference surface and the height sensor is within the range of detection for the height sensor;

FIG. 25C shows the nvCPD sensor moved slowly down while the level of the nvCPD signal is monitored;

FIG. 25D shows that if the desired height is h*, then the height sensor is positioned above the surface so that the surface is within the measurement range of the height sensor;

FIG. 25E illustrates that the nvCPD sensor is height adjusted to $z^*=z3-(h3-h1)-(z1-z2)+h^*$, which results in a height of the nvCPD sensor probe tip above the surface of h*;

DETAILED DESCRIPTION OF THE PREFERRED EMBODIMENTS

Figure 1:
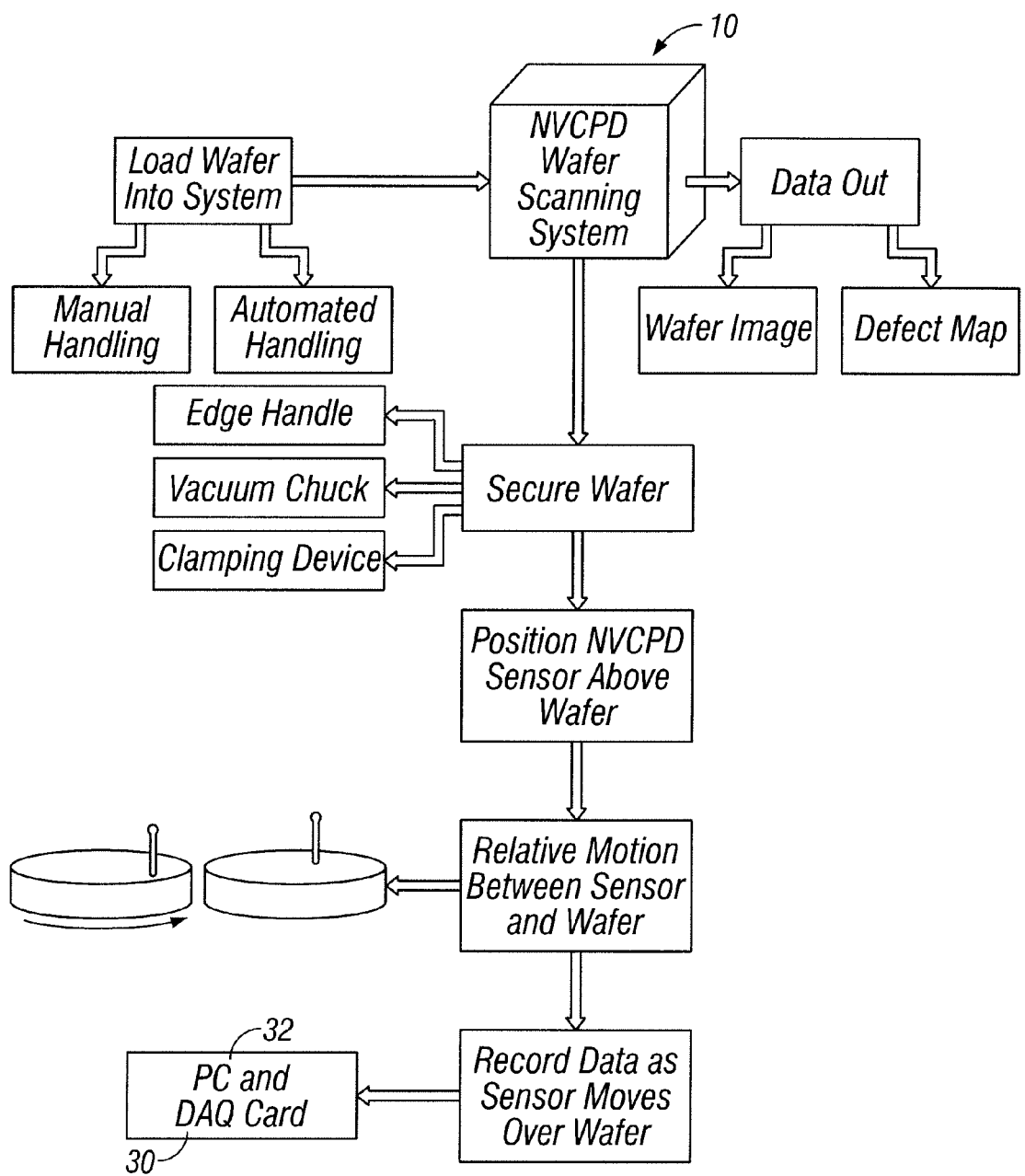
FIG. 1 illustrates one embodiment of the nvCPD scanning method and system.

A contact potential difference sensor is an important part of the invention described herein and thus we will describe first the basis of operation of the sensor which relates to work function. The work function of an electronic conductor is defined as the minimum amount of work required to move an electron from the interior of the conductor to a non-interacting point outside the surface (beyond the image charge region). The work function is a fundamental property of a material surface; and as such, it is of interest in a wide range of surface phenomena. The work function of a particular material will vary if contaminants or coatings are present (or absent). These variations can be used to determine the cleanliness of a surface, the uniformity or thickness of a coating, and other information about the condition of the surface. Work function measurement is of use in the study of semiconductor doping, organic semiconductors, organic monolayers, surface reactivity, biological systems, heterogeneous catalysis, and corrosion.

The work function of a surface is typically measured using a vibrating Kelvin probe. A vibrating Kelvin probe operates by measuring Contact Potential Difference (CPD), which is the potential that forms between two materials with different work functions when they are electrically connected. Thus, a vibrating Kelvin probe is also referred to as a vibrating contact potential difference (vCPD) probe or sensor. Two different metals, with different work functions and Fermi levels are placed in close proximity, but not connected. If the two metals are then electrically connected, electrons will flow from the material with the smaller work function ($\Phi_1$) to the material with the larger work function ($\Phi_2$), resulting in an accumulation of charge on the two metals and the formation of an electric field between them. The electric potential is termed the CPD and is proportional to the work function difference. The amount of charge that is formed is equal to the product of the capacitance between the two metals and their CPD. The vCPD probe operates by measuring the CPD between a probe of known work function and a surface of unknown work function. The probe can be vibrated over the surface to be measured. This vibration causes a periodic variation in the capacitance between the two materials, which results in a time-varying current into the probe. This current is measured and nullified by applying an opposing voltage on the probe or surface. This voltage, known as the backing potential, results in zero current when it is equal to the CPD between the two materials.

The vCPD probe has been used in a wide variety of applications. These include the measurement of dielectric layer thickness and contamination inside the dielectric layer. Such probes can be used to form images of work function variation across surfaces, but the need to vibrate the probe and adjust the backing potential results in limited data acquisition rates that are not compatible with fast cycle time, high resolution imaging applications.

The non-vibrating contact potential difference (nvCPD) measurement technique is an important improvement of the traditional vCPD probe method. Instead of vibrating the probe, the nvCPD sensor detects work function variations by translating the probe relative to the sample surface. Variations in work function across the surface result in variations in CPD and the associated voltage between the probe and the surface. These voltage variations produce a small current into the probe that can be amplified and sampled. The use of translation instead of vibration results in a dramatic improvement in the data acquisition rate. While vCPD probes typically acquire data at a maximum of several samples per second, the nvCPD probe can acquire data into the millions of samples per second, making it suitable for high speed imaging applications. In fact, faster relative motion between the probe and the surface of the wafer results in an increase in signal strength (within the bandwidth limits of the amplifier). The increased scanning speed of the nvCPD sensor is critical for its use as an in-line tool for contamination detection during semiconductor manufacturing. The nvCPD sensor generates relative CPD data while the vCPD sensor generates absolute CPD data.

In both the vibrating and non-vibrating CPD sensors, the sensor probe and the measured surface form a capacitor. The well-known formula for the charge on a capacitor is simply:

$$Q = CV$$

where Q is charge, C is capacitance and V is voltage. The current, i, into a capacitor is obtained by differentiating the prior equation:

$$i = \frac{dQ}{dt} = C\frac{dV}{dt} + V\frac{dC}{dt}$$

For both vibrating and non-vibrating sensors, the voltage across the capacitor is the CPD resulting from the difference in work function between the probe and surface. However, the vibrating probe determines the CPD by applying a backing voltage to zero the current during vibration. The resulting backing voltage is equal in magnitude, and opposite in sign, to the CPD.

$$i = (V_{cpd} + V_b)\frac{dC}{dt}$$
$$i = 0 \text{ when } V_b = -V_{cpd}$$

The non-vibrating probe, however, detects changes in voltage across the capacitor while the probe moves relative to the surface. If the surface is relatively smooth and the gap between the probe and surface is relatively constant, then the capacitance is constant, and the resulting current into the probe is given by:

$$i = C\frac{dV_{cpd}}{dt} = C\frac{dV_{cpd}}{dx}\frac{dx}{dt} = Cv\frac{dV_{cpd}}{dx}$$

where v is the relative velocity of the probe and underlying surface, dx represent the change in relative position. Any variation in CPD generates a current into the probe. Since the work function of the probe is fixed, the probe signal is proportional to work function variation across the surface.

Figure 2:
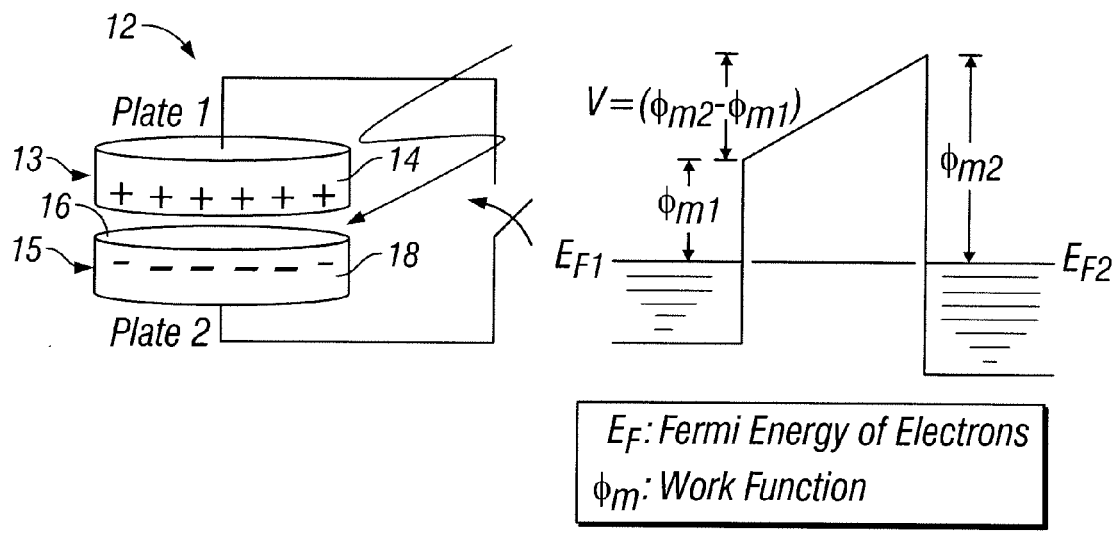
FIG. 2 illustrates the concept of the contact potential difference methodology.

A preferred embodiment of the invention is directed to an improved use of an nvCPD sensor. In particular, FIG. 1 illustrates a functional block flow diagram of components and operation of one preferred form of an nvCPD scanning system 10. A nvCPD sensor 12 (see FIG. 2) is based on the phenomena of contact potential difference which is a voltage generated between two dissimilar materials brought in close proximity to each other. An illustration of this concept can be seen in FIG. 2. In the case of a wafer scanning system 10, the sensor tip 13 forms a first plate 14 and a wafer 15 having a wafer surface 16 forms a second plate 18 (see FIG. 2). Probe tip surface 20 of the first plate 14 is made of a conducting material with a fixed work function—generally, the difference in energy between the Fermi level of the solid and the free energy of the space outside the solid, including, in metals, the image potential of electrons just outside the surface. The wafer surface 16 of the second plate 18 has a work function which can vary due to irregularities in the semiconductor wafer surface 16 or contaminants or other materials deposited on the wafer surface 16. When the first plate 14 and the second plate 18 are electrically connected, the Fermi levels of the respective surface equilibrate and form an electric field between them. If the work function of the sensor tip 13 is fixed, the magnitude of the electric field is then related to the distance between the first plate 14 and the second plate 18, the relative dielectric between the first plate 14 and the second plate 18 and the work function of the wafer surface 16. In practice the first plate 14 and the second plate 18 equilibrate rapidly providing little to measure. To provide a current flow that can be measured, some motion of the sensor tip 12 relative to the wafer surface 16 must be realized. In one embodiment, the nvCPD sensor 12 is moved over the surface at a substantially fixed distance and variations in the wafer surface 16 cause a current to flow.

Figure 3:
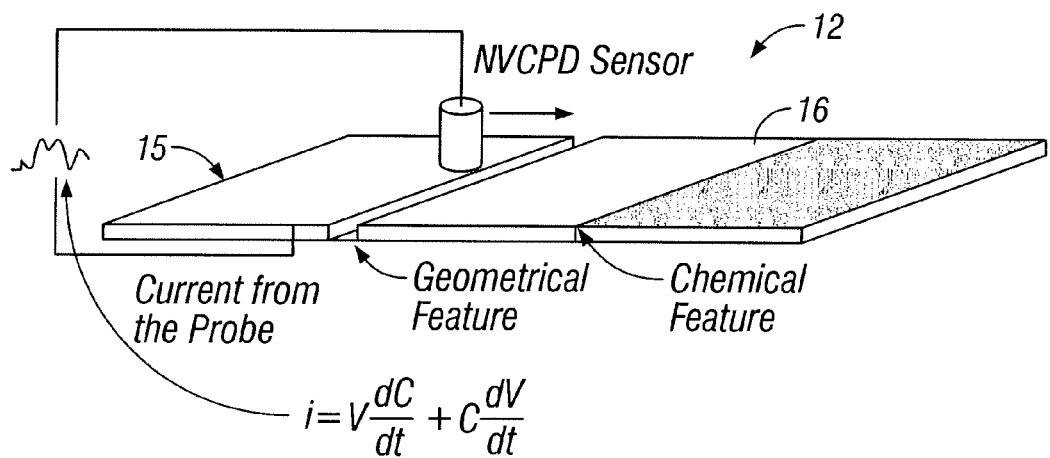
FIG. 3 illustrates an nvCPD scanning method.

An illustration of this concept can be seen in FIG. 3. The current flow from this nvCPD sensor 12 can be modeled by the following equation:

$$i = C\frac{\partial V}{\partial t} + V\frac{\partial C}{\partial t}$$

wherein C and V are defined as $$C = \frac{\varepsilon_o \varepsilon_r A}{d} \text{ and } V = \frac{\Phi_{probe} - \Phi_{wafer}}{|e|}$$

and further wherein $\varepsilon_o$ is the permittivity of free space, $\varepsilon_r$ is the relative dielectric constant, A is the area of the probe tip, d is the distance between the sensor tip 13 and the wafer 15, Φ is the work function of the respective surface, and e is the charge on an electron. The V term can also be described as a difference in surface potentials between the nvCPD sensor 12 and the wafer 15. In addition the surface potentials on the wafer surface 16 can vary due to defects. The overall surface potential is related to the underlying materials work function, but it can also be affected by adsorbed layers of material on the wafer surface 16. Even sub mono-layers of materials are known to significantly affect the surface potential.

Figure 4:
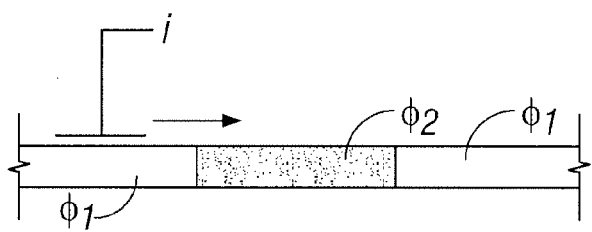
FIG. 4 illustrates the current output of an nvCPD probe as it passes over a positive and negative work function transition.
Figure 4:
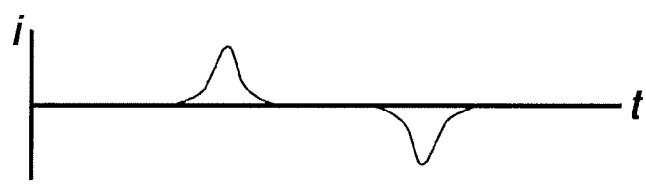

The $$C\frac{\partial V}{\partial t} \approx C\frac{\Phi_{probe} - \Phi_{wafer}}{\Delta t}$$

term is related to changes in work function on the wafer surface 16. It can be seen that the magnitude of this term is related to the relative changes in work function on the wafer surface 16 and relative speed at which the nvCPD sensor 12 is moved over the wafer surface 16. An illustration of the signal generated from this can be seen in FIG. 4. Thus, a system in accordance with the principles of the present invention is capable of generating one-dimensional signals and two-dimensional images, although three-dimensional images can be generated.

Many defects can present themselves as variations in the wafer (or other material surface) work function or the overall surface potential. Both chemical and physical (i.e., geographical) features of the wafer surface and the underlying materials can affect the work function of a particular portion or even a single point on the wafer surface; thus, these features can be detected by a sensor in accordance with the principles of the present invention. For instance, variation in semiconductor dopant concentrations in the wafer 15 will cause varying characteristic work functions. In addition, other materials that could diffuse into the wafer 15, such as but not limited to copper, will cause variations in work function. Within the semiconductor material (or any other material susceptible to measurement) itself, mechanical phenomena such as dislocation pile-ups, cracks, and scratches generate local stresses which will change the local work function. In addition, adsorbed layers of atomic or molecular contaminants even at the sub monolayer level will generate appreciable surface potential variations. Particles deposited on the wafer 16 with a surface potential different than the surrounding wafer material will also create a signal. Layers of chemicals commonly used in the wafer fabrication process will affect the surface potential of the wafer. For instance residual CMP slurry or photo-resist would cause local variations in surface potential detectable by the nvCPD sensor 12 of the present invention. Such defects and chemistry have associated with them characteristic signatures which enable inspection of the wafer surface.

The $$V\frac{\partial C}{\partial t}$$

term is related to changes in gap between the nvCPD sensor 12 and the wafer 15 or variations in the relative dielectric constant. Geometrical imperfections in the wafer surface 16 or particles on the wafer surface 16 would manifest themselves in this component. Also because of its differential nature, the magnitude of this component would also increase as the relative speed of the nvCPD sensor 12 to the wafer 15 is increased.

As previously mentioned, physical or geographical aspects and defects can be imaged using a system in accordance with the principles of the present invention. Many classes of wafer defects would appear as geometrical changes in the wafer surface 16. In the wafer 15 itself, surface cracks, scratches and etched trenches would be nonlimiting examples of such defects causing a geometrical change in the wafer surface and an attendant change in the work function. In addition, particles deposited on the wafer 15 would also present themselves as a local change in the distance to the probe sensor tip 13.

Variations of dielectric films on the wafer 15 can also be detected. An example would be detecting variations in the oxide state grown on the silicon substrate (i.e. $SiO$, $SiO_2$, $SiO_3$, $SiO_4$). In addition, variations in dielectric of other nonconducting materials commonly deposited on the wafer could be detected.

It should also be noted that many features could present themselves as combinations of geometrical changes and chemical changes. For instance, a particle deposited on the wafer 15 of differing material than the underlying wafer 15 could cause variation in material surface properties. Also, a crack in the surface would also induce stresses that would cause variations in local work function.

Figure 5:
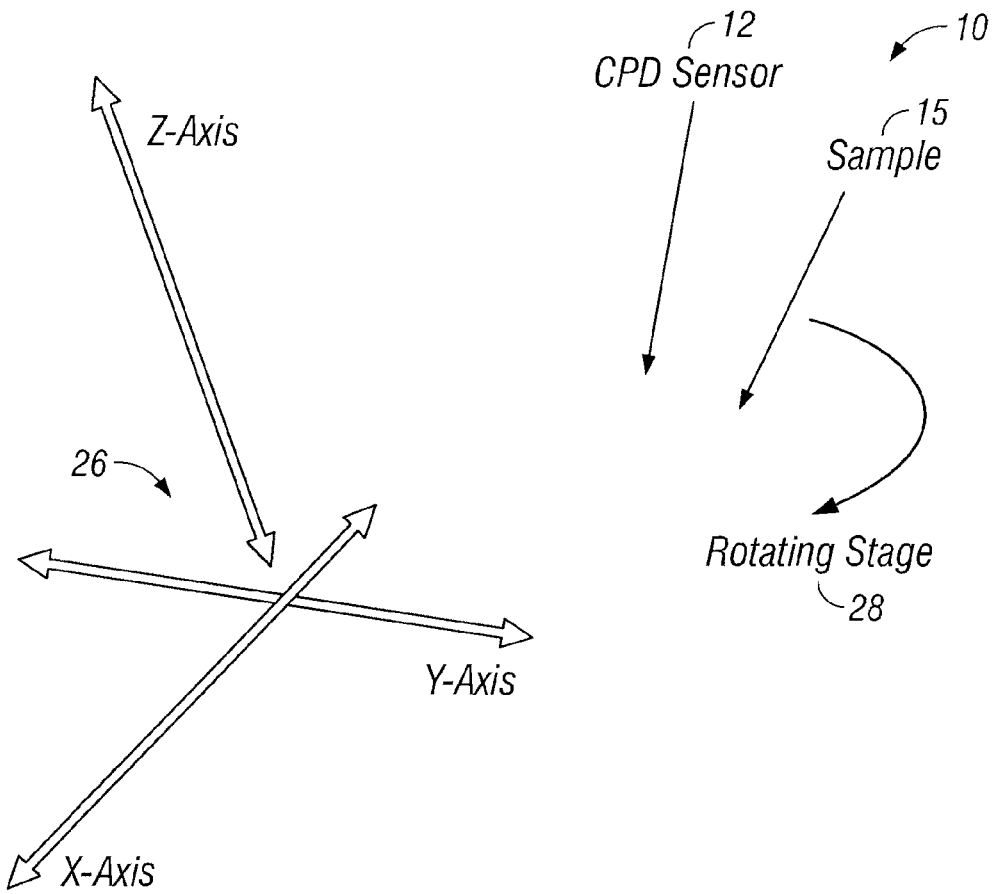
FIG. 5 illustrates axial orientation of the nvCPD system.
Figure 8A:
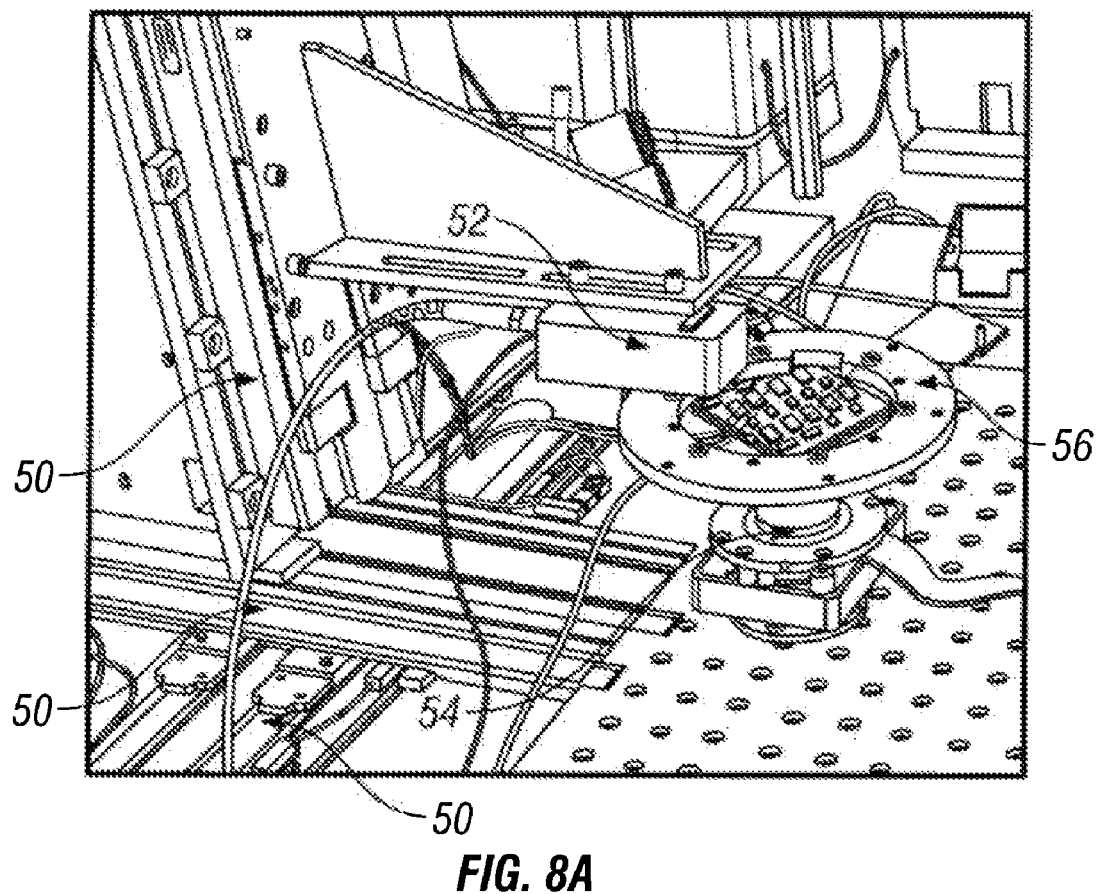
FIG. 8A illustrates one form of scanning nvCPD system with a three axis linear positioning system with the nvCPD sensor and a wafer mounted on a high speed spindle.
Figure 8B:
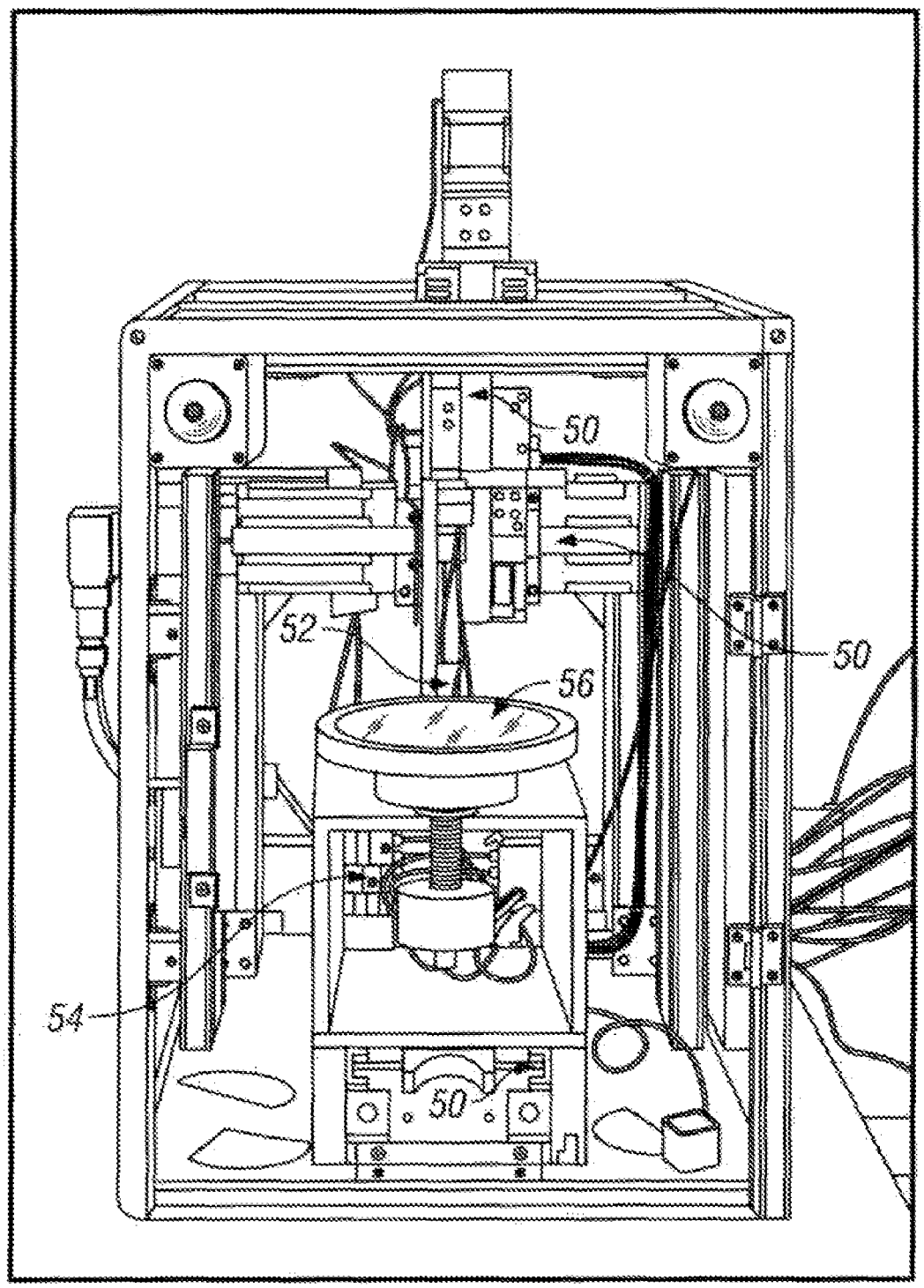
FIG. 8B illustrates another form of scanning nvCPD system.

In FIG. 5 is schematically shown one form of the system 10 for application of the nvCPD sensor 12 to scan the wafer 15 for defects and contamination. FIGS. 8A and 8B also illustrate more detailed drawings of two alternative operating embodiments of the system 10. The system 10 in FIG. 5 includes an X-Y-Z positioning system 26, a rotating wafer stage 28, a high speed data acquisition system 30 with a personal computer (PC) 32, and control software executed by the PC 32.

Figure 21A:
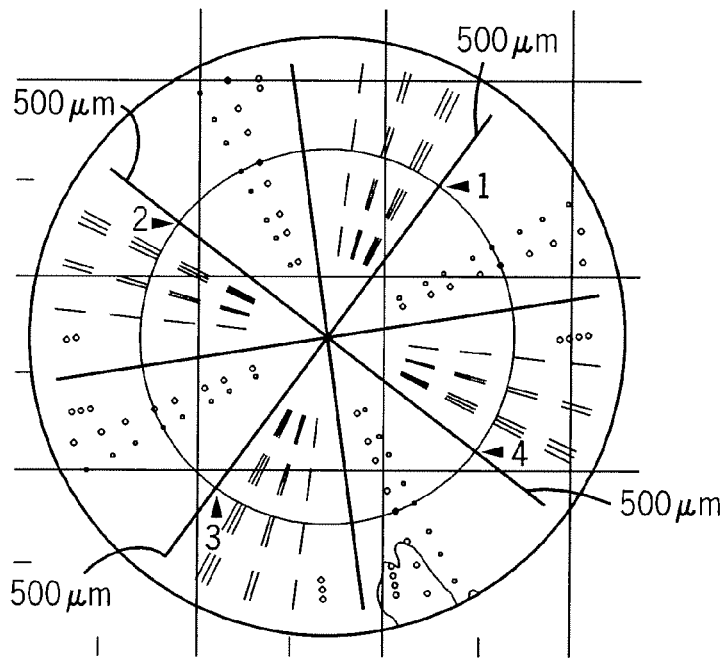
FIG. 21A illustrates a wafer map produced in accordance with the principles of the present invention, wherein the wafer pattern is one atomic layer thick over native silicon oxide.
Figure 21C:
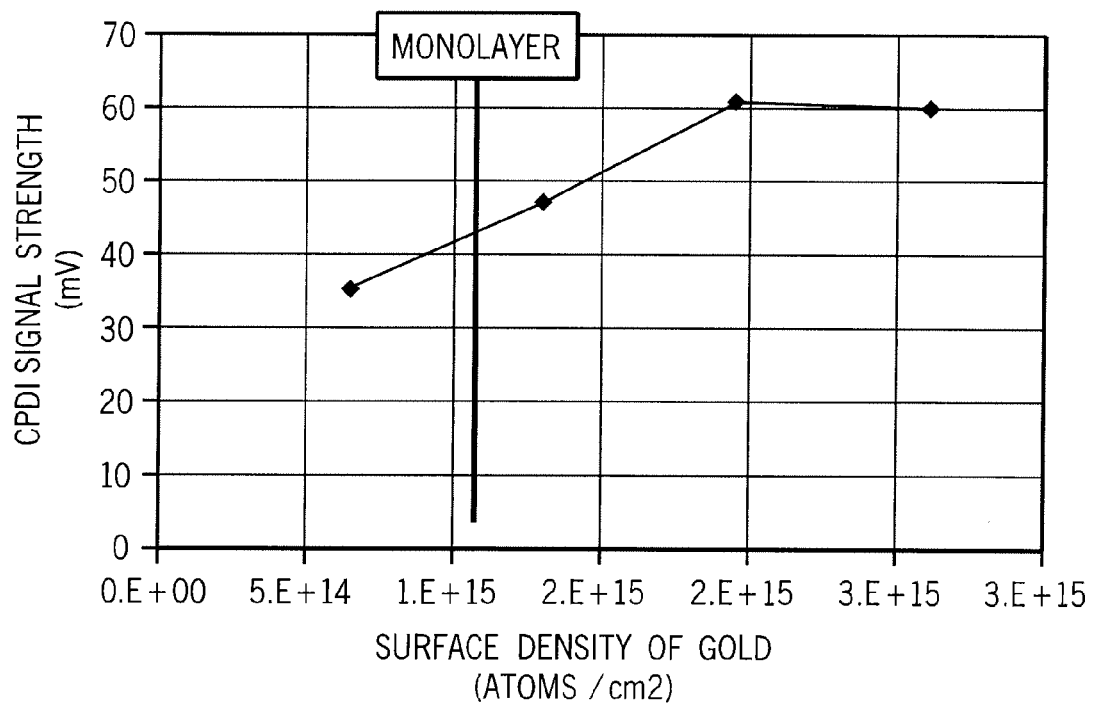
FIG. 21C is a graph of the signal strength versus the density of gold for the wafer map depicted in FIG. 21A.
Figure 21B:
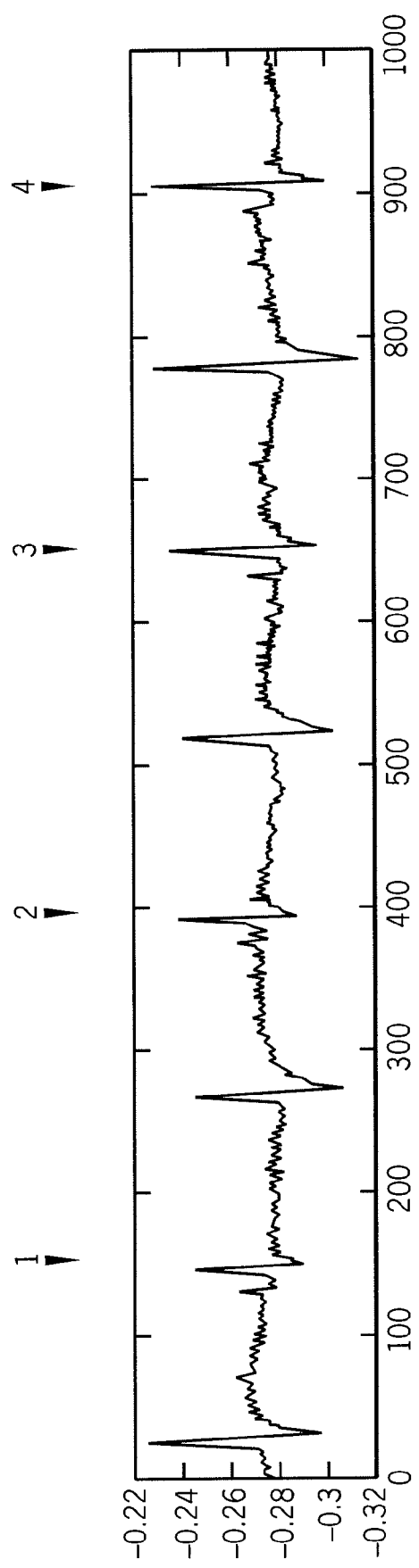
FIG. 21B is a graph showing signal strength along a single probe track.

As shown in more detail in FIG. 8A, in one embodiment, the wafer 15 is affixed to a rotating spindle or chuck 54 (see FIG. 1) using a clamping fixture 56 on the wafer edges. In a preferred embodiment, a vacuum clamping mechanism is used with the sample stage. A sensor positioning system 50 includes an nvCPD sensor 52 positioned a fixed distance from the wafer 15 is mounted to a spindle 54. The wafer 15 (not seen in this view) is then rotated at high speed, and the nvCPD sensor 52 is translated radially to collect data in circumferential tracks. The scanning procedure as shown schematically in FIG. 9 lasts between a few seconds and several minutes, depending on the number of scanned tracks, the speed of the spindle 54, and the speed of the sensor positioning system 52. The tracks of data are then put together to form a CPD image. These CPD images allow the visualization of chemical and geometrical defects and thereby enable classification of the type of defect present on the wafer surface. Some examples of these CPD images can be seen in FIG. 10A-15 and are taken from a 100 mm wafer compared with optical images of the same wafer (see, Example 1 infra). The present invention is capable of generating image maps of one atomic layer thick patterns, as shown in FIG. 21A. FIG. 21B illustrates the signal strength as the wafer is rotated relative to the probe, thus passing over defects and features of the wafer surface. As shown in FIG. 21C, the present invention, in fact, detected sputtered gold at densities less than a single complete atomic layer.

Figure 6:
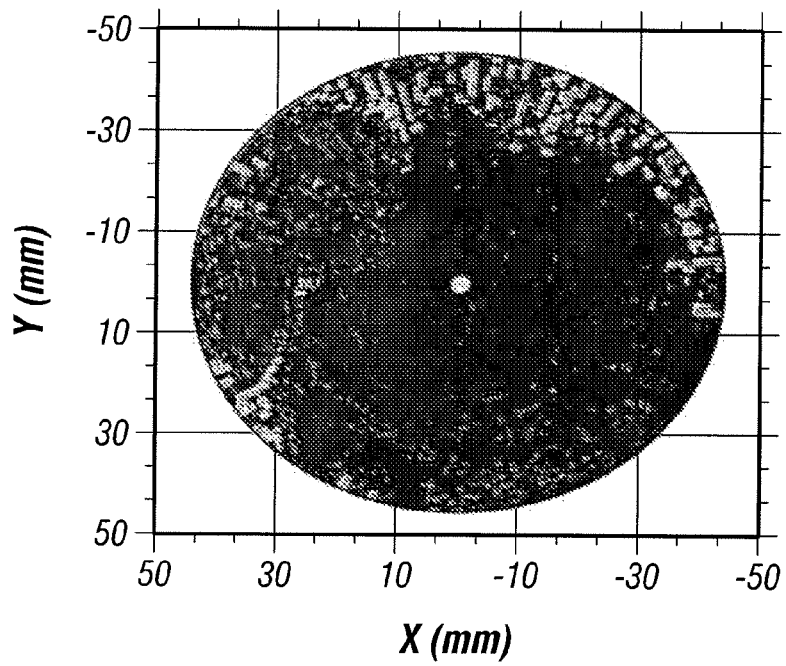
FIG. 6 illustrates standard deviation of signals within a scan area.
Figure 9:
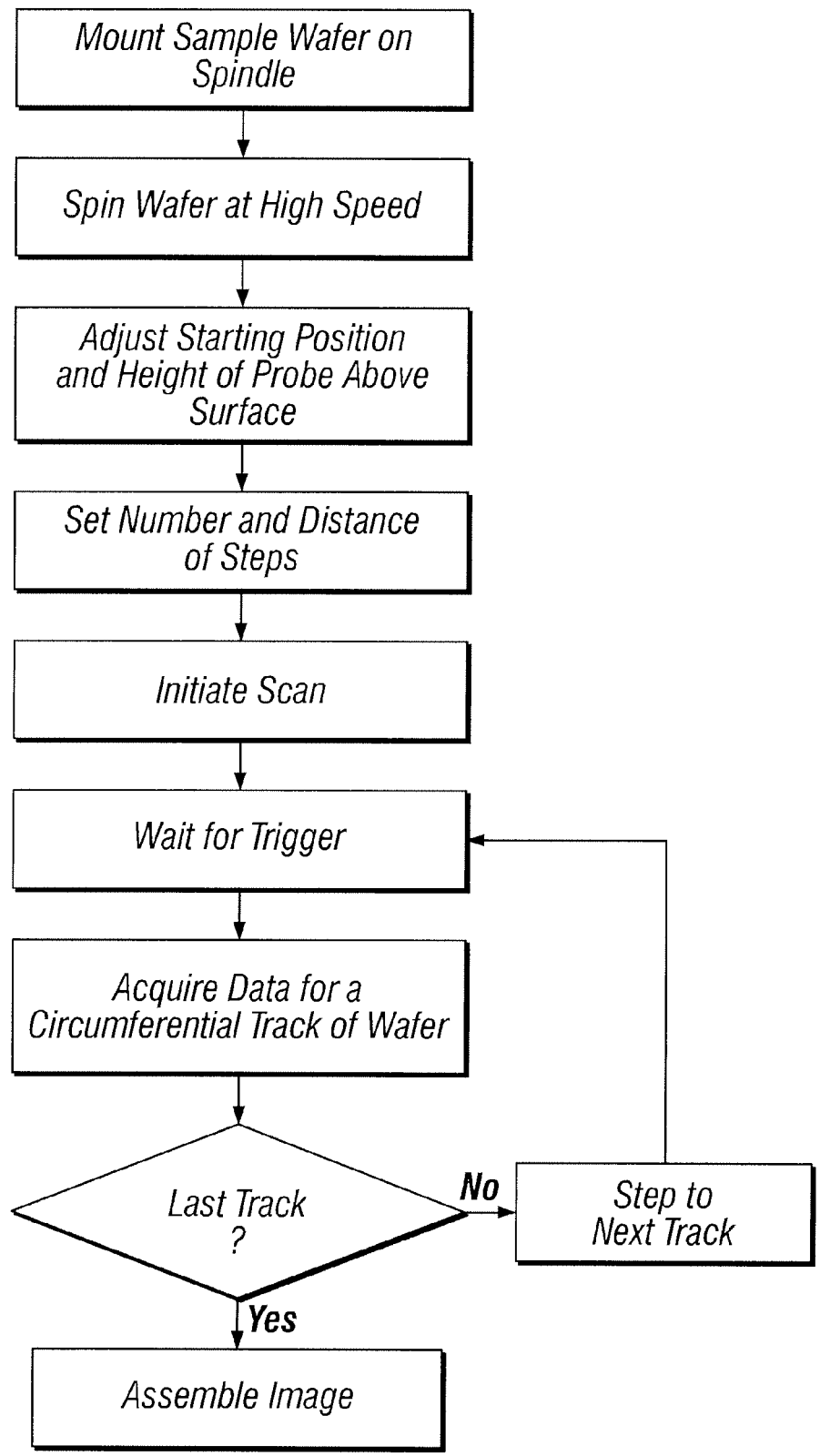
FIG. 9 illustrates a flow diagram for the image acquisition process of a radially scanned nvCPD imaging system.

The images generated by the scanning procedure of FIG. 9 were subsequently processed to automatically locate defects; thus locating areas of high variability. An ideal surface would exhibit a flat signal, but a wafer surface with defects would exhibit some variability in the signal. To locate areas with defects, the data was broken up into small areas of known location. The standard deviation of the signal within these areas was determined. Areas with defects showed a higher standard deviation, and these results can be seen in FIG. 6. Areas with defects appear brighter than lower variability areas of the wafer 15. This is one of many possible methods in accordance with the principles of the present invention to process the sensor data.

More generally, a defect can be identified by one or more of the following methods:
   Process the data to look for a voltage or change in voltage (or pattern of voltages or changes in voltages) that exceeds some user-defined value (threshold).
   Compare the data to a known pattern that represents a defect via some form of correlation or template matching.
   Convert the spatial data to the frequency domain and then identify peaks in the frequency domain that represent defects with unique spatial characteristics.

These techniques can also be combined with other techniques to yield analytical results. The signal may also be preprocessed to facilitate defect detection, such as, for example:
   Since the signal is differential, it can be integrated over some distance to produce voltages that represent relative CPD's over the surface of the wafer 15.
   If the wafer 15 is "patterned", then this known pattern can be removed from the data prior to processing. This would likely be accomplished through some conventional method of variation of image or signal subtraction in either the space or frequency domains.
   The signal would likely be processed with some form of frequency filtering to remove high or low frequencies depending on the size, shape and other characteristics of the expected defects.
   The signal could be processed to remove features of a certain size by doing what is called "morphological processing" which is by itself well known in other applications.

Figure 22A:
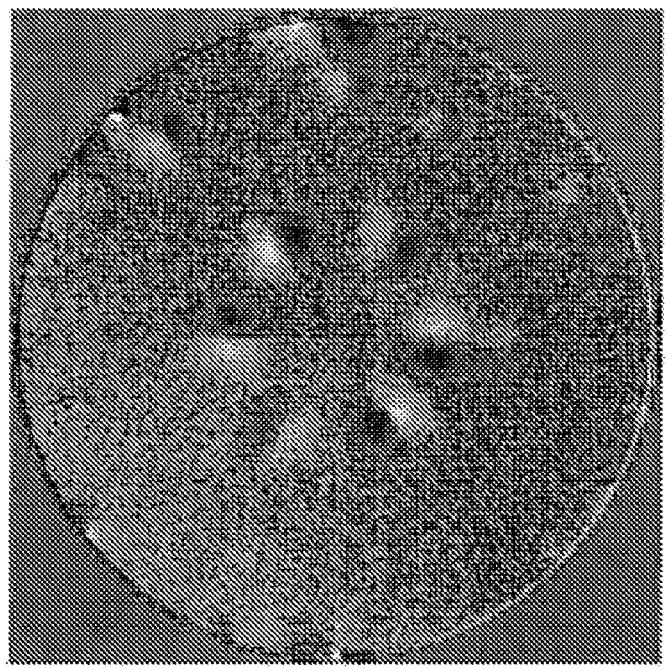
FIG. 22A is a 2-D Edge Detection optical view using Canny Algorithm at Multiple Resolutions (#7 Wafer dipped into a CMP Slurry)
Figure 22B:
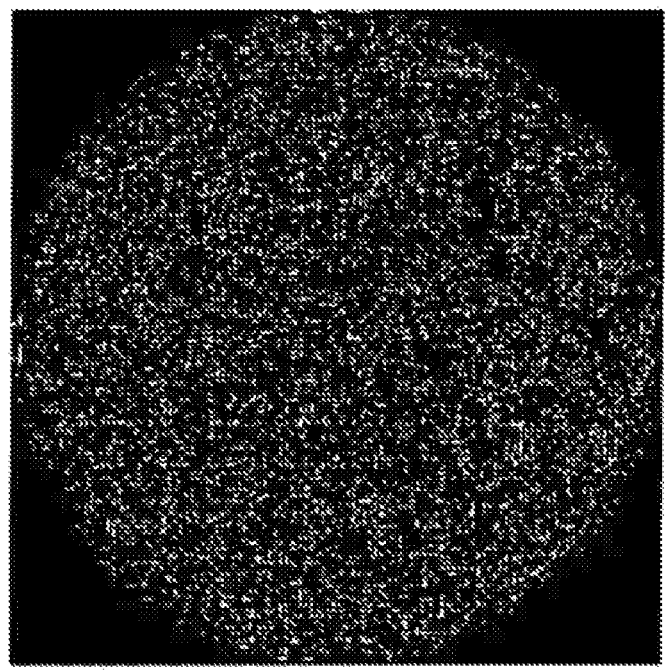
FIG. 22B is a 2-D Edge Detection image produced in accordance with the principles of the present invention using Canny Algorithm at Multiple Resolutions (#7 Wafer dipped into a CMP Slurry, threshold=0.00001, Contamination Level=24.5)
Figure 22C:
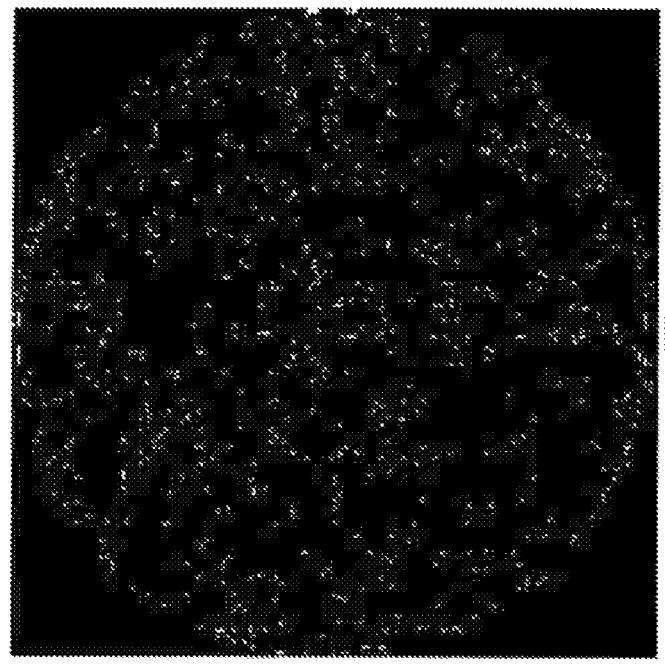
FIG. 22C is a 2-D Edge Detection image produced in accordance with the principles of the present invention using Canny Algorithm at Multiple Resolutions (#7 Wafer dipped into a CMP Slurry, threshold=0.008, Contamination Level=4.5)
Figure 22D:
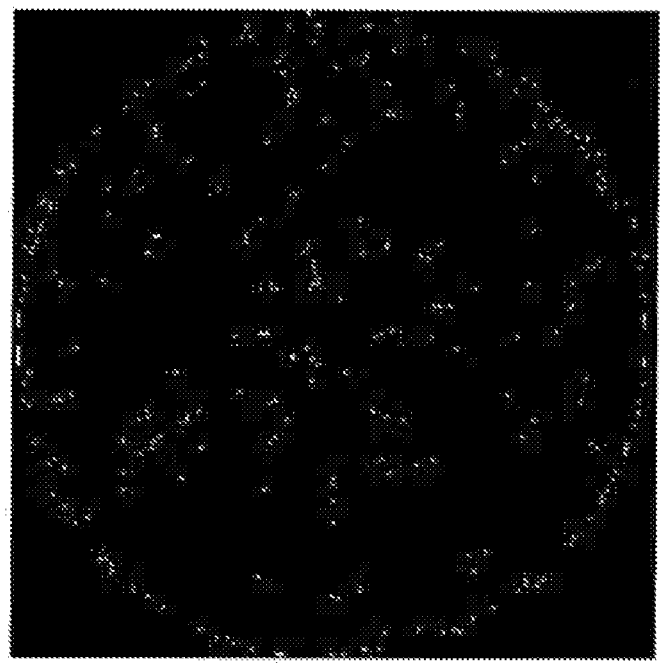
FIG. 22D is a 2-D Edge Detection image produced in accordance with the principles of the present invention using Canny Algorithm at Multiple Resolutions (#7 Wafer dipped into a CMP Slurry, threshold=0.01, Contamination Level=1.9)
Figure 22E:
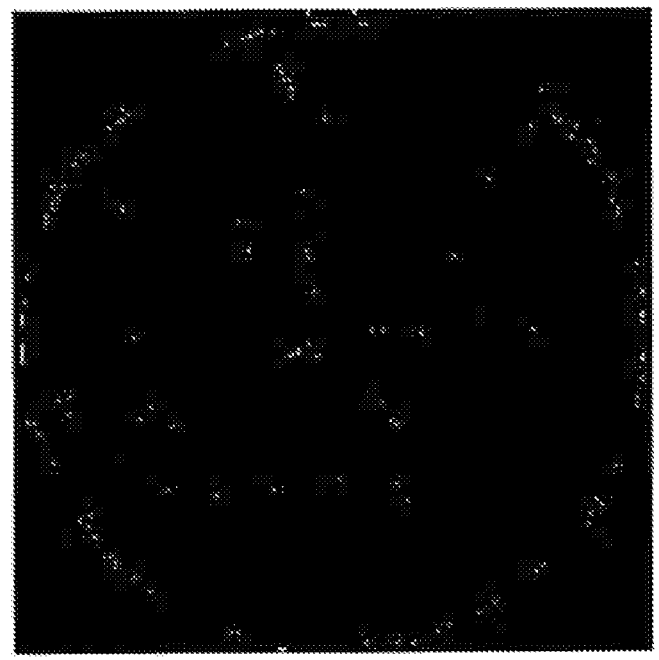
FIG. 22E is a 2-D Edge Detection image produced in accordance with the principles of the present invention using Canny Algorithm at Multiple Resolutions (#7 Wafer dipped into a CMP Slurry, threshold=0.012, Contamination Level=1.1)
Figure 22F:
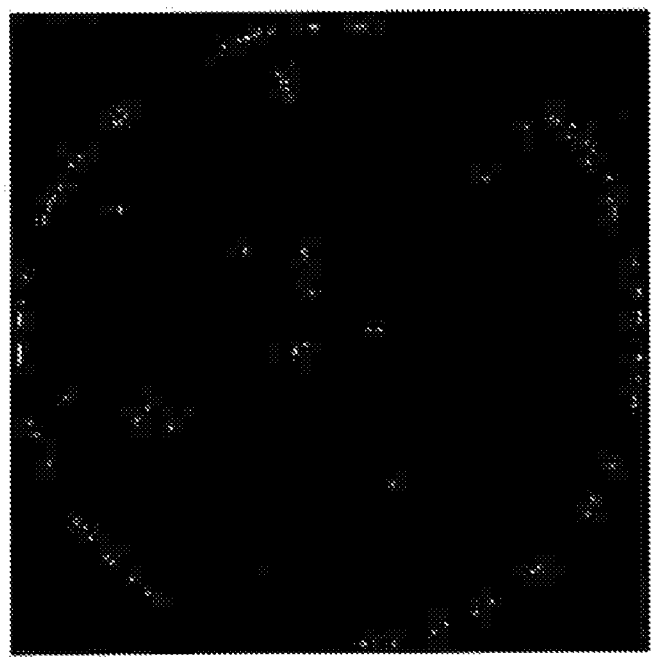
FIG. 22F is a 2-D Edge Detection image produced in accordance with the principles of the present invention using Canny Algorithm at Multiple Resolutions (#7 Wafer dipped into a CMP Slurry, threshold=0.014, Contamination Level=0.8)
Figure 23A:
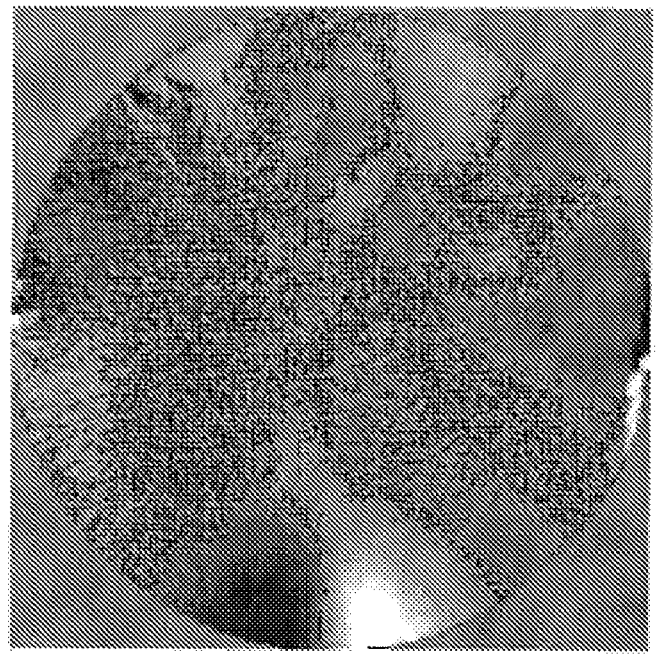
FIG. 23A an optical image of 2-D Edge Detection produced in accordance with the principles of the present invention using Canny Algorithm at Different Scales (Qcept #6 Wafer dipped into a CMP Slurry)
Figure 23B:
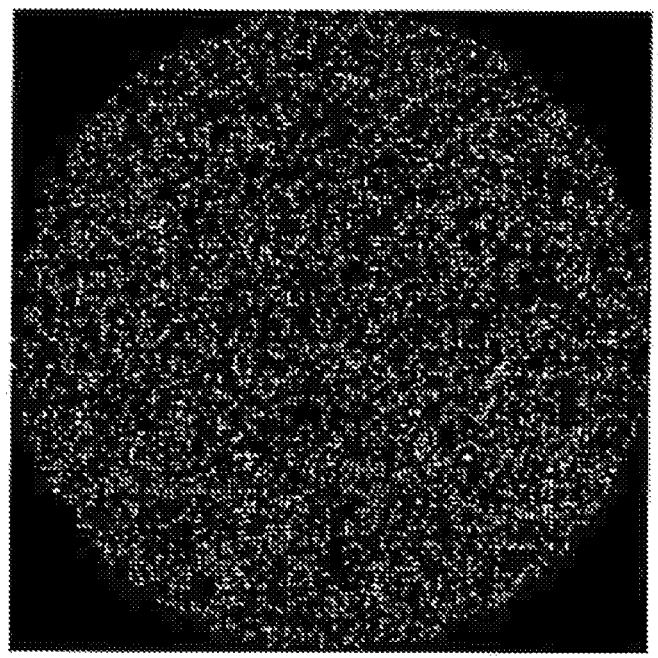
FIG. 23B an optical image of 2-D Edge Detection produced in accordance with the principles of the present invention using Canny Algorithm at Different Scales (Qcept #6 Wafer dipped into a CMP Slurry, threshold=0.00001, Contamination Level=24.3)
Figure 23C:
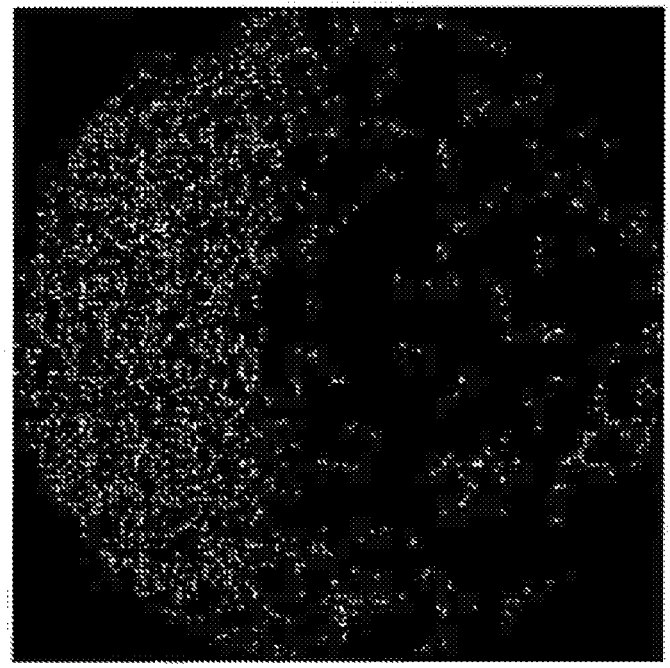
FIG. 23C an optical image of 2-D Edge Detection produced in accordance with the principles of the present invention using Canny Algorithm at Different Scales (Qcept #6 Wafer dipped into a CMP Slurry, threshold=0.005, Contamination Level=9.6)
Figure 23D:
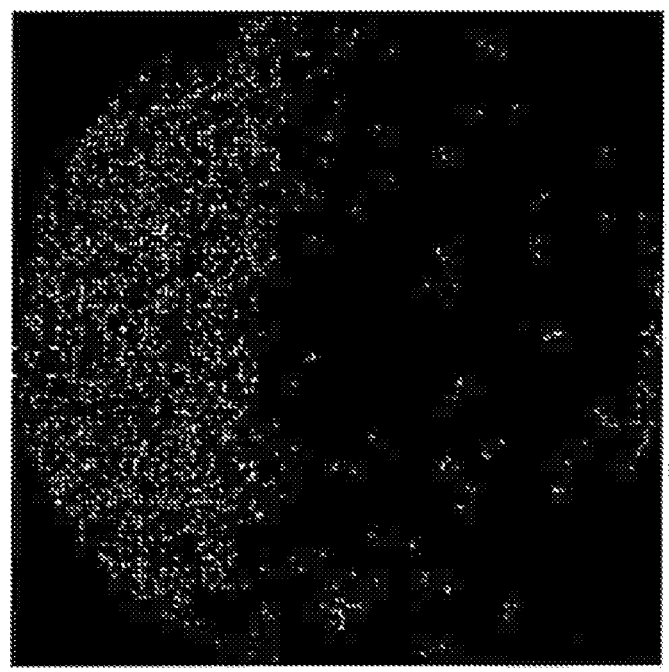
FIG. 23D an optical image of 2-D Edge Detection produced in accordance with the principles of the present invention using Canny Algorithm at Different Scales (Qcept #6 Wafer dipped into a CMP Slurry, threshold=0.006, Contamination Level=8.2)
Figure 23E:
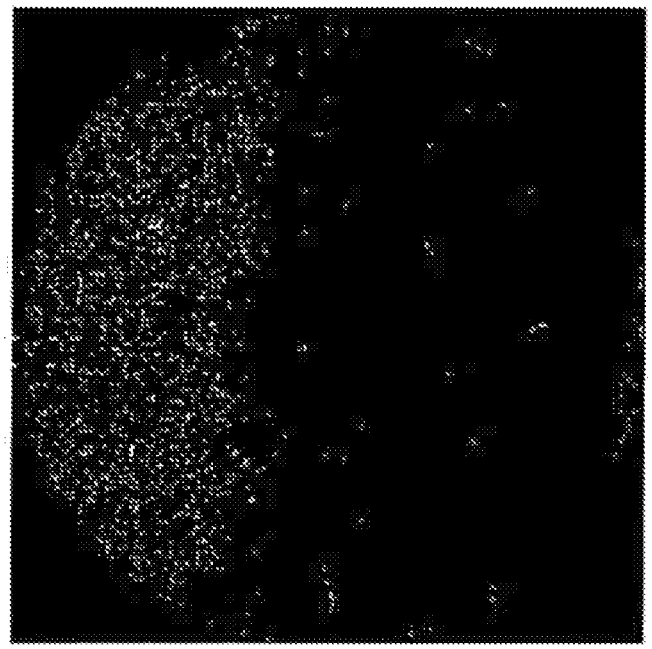
FIG. 23E an optical image of 2-D Edge Detection produced in accordance with the principles of the present invention using Canny Algorithm at Different Scales (Qcept #6 Wafer dipped into a CMP Slurry, threshold=0.008, Contamination Level=6.9)
Figure 23F:
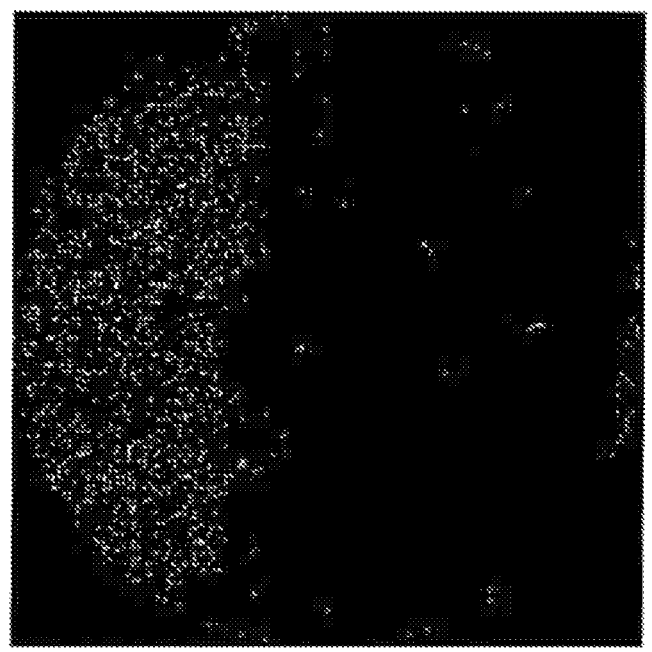
FIG. 23F an optical image of 2-D Edge Detection produced in accordance with the principles of the present invention using Canny Algorithm at Different Scales (Qcept #6 Wafer dipped into a CMP Slurry, threshold=0.009, Contamination Level=6.4)

In one embodiment, a defect is detected and the contamination level is quantified based on an edge detection algorithm, such as but not limited to a Canny Edge detection algorithm. Multiple resolutions may be used or multiple scales or a combination thereof. FIGS. 22B-F depict the edge detection at various resolutions and is shown in comparison to an optical image (FIG. 22A). FIGS. 23B-F depict edge detection at various scales and in comparison to an optical image (FIG. 23A). In a preferred example of such an embodiment, the contamination or defect is detected and quantified using the steps of:
   Generating a CPD sensor peak signal at the boundary between two different areas (The peak signals behave much like the "edges", an image processing term. So, the contaminated area can be located by edge detection.);
   Apply an Edge detection algorithm (such as the 2D Canny algorithm);
   Multiple resolutions with different thresholds (thereby enabling detection of various size of contaminants, i.e. the higher resolution (lower threshold) will find the smaller contaminants); and
   Quantifying contamination level (CL) by the edge area over the total wafer area in the simplest way.

As previously discussed, determining a reference point for the sensor is necessary for optimal results. In one embodiment, the reference point is at the center of rotation (in the X-Y plane) and at the height of the surface of the wafer (on the Z axis). To find this point, the center of rotation and the height of the surface of the wafer must be determined, and then the height sensor is correlated with the Z position of the nvCPD sensor.

To find the center of rotation, the nvCPD sensor and motion system are used to find a geometrical and/or chemical feature on the surface of the spinning wafer at three or more points. Since the wafer is spinning, the feature describes a circle. The center of the circle is the center of rotation. Given the coordinates of three distinct points $(A(x_1,y_1), B(x_2,y_2),$ and $C(x,y))$ on the diameter of the defined circle on the circle, its center is found algebraically by the equation:

$$(x-x_1)((x-x_2)+(y-y_1)(y-y_2))=0.$$

Due to slight measurement errors, a different set of points might yield slightly different center coordinates. The "true" center of rotation is deemed to be the locus (average) of these points.

In one embodiment, to find the height of the surface of the wafer without touching the wafer surface, two sensors, the nvCPD sensor and a height sensor (which could itself be an nvCPD sensor in an embodiment discussed below) can be used. The nvCPD sensor and height sensor are calibrated so that when a reading is taken with the height sensor, the Z-axis coordinate of the tip of the nvCPD sensor is ascertained. (This calibration procedure is described below.) At that point, the readings of the height sensor are correlated with the Z position of the nvCPD sensor. Thereafter, the height sensor is used to detect the position of the surface of the wafer without touching it, and then the tip of the nvCPD sensor positioned accordingly.

In one embodiment, the height sensor is correlated with the Z position of the nvCPD sensor based on two assumptions: first, that within its usable range, measurements from the height sensor are linear in the Z axis and that a constant, k, can map changes in height measurements to proportional changes in Z; and second, that the relative positions of the height sensor and nvCPD sensor are fixed, i.e. the two sensors can move relative to the rest of the world but only as a unit; they, therefore, cannot move independently. Based on these assumptions, a point, P, is picked in the X-Y plane where calibration is to be performed. The height sensor is positioned above P, and a measurement from the height sensor, $H_m$, correlated with a coordinate on the Z axis, $Z_h$. Next the nvCPD sensor is positioned above P and moved down until it touches at a point, $Z_c$. The nvCPD signal changes significantly when the sensor tip touches the surface. Once these values are known, the Z value of the point where the tip of the nvCPD sensor would touch the surface is derived with the following equation:

$$Z_{surface}=Z_{current}+Z_c-Z_h+(H_m-H_{current})/k$$

wherein:
$Z_{surface}$ is the height of the surface where the tip of the nvCPD sensor would touch;
$Z_{current}$ is the current height of the sensor; and
$H_{current}$ is the current height sensor measurement.

As previously mentioned, the height of the sensor should be measured and controlled to produce repeatable results. It is also possible to use an nvCPD sensor to control the height in a semiconductor wafer inspection system in accordance with the principles of the present invention. In order to use the nvCPD sensor to control height, the system must provide the capability to apply a time-varying bias voltage between the probe tip and the wafer surface. As the bias voltage varies, it produces an output signal that is a function of the capacitance between the probe tip and the wafer surface. The closer the probe tip is to the surface, the larger the output voltage. After the relationship between height and capacitance is determined, the magnitude of the output signal can be used to calculate the height of the sensor. The signal magnitude can be calculated as the peak-to-peak, standard deviation, RMS, or some other measure known in the art.

Again, the formula for the output of the nvCPD sensor is:

$$i = C\frac{\partial V}{\partial t} + V\frac{\partial C}{\partial t}$$

The voltage V is the contact potential difference between the probe tip and the wafer surface. If a bias voltage is applied, the formula then becomes:

$$i = C\frac{\partial (V + V_b)}{\partial t} + (V + V_b)\frac{\partial C}{\partial t}$$

where $V_b$ is the bias voltage. If the nvCPD sensor is not moving relative to the surface of the wafer (or is moving relatively slowly), then the capacitance C and the contact potential difference voltage V are not changing, and the equation becomes:

$$i = C\frac{\partial V_b}{\partial t}$$

Since the bias voltage is a known fixed frequency and magnitude, the output current is a function of the capacitance (C). C is a combination of the capacitance between the probe tip and wafer surface, and any stray capacitances in the circuit. The capacitance vs. height function can be characterized and used to determine the height of the nvCPD probe at a point above the wafer surface. Once the height of the sensor is determined, then the bias voltage can be turned off in order to make scanning nvCPD measurements.

Figure 18:
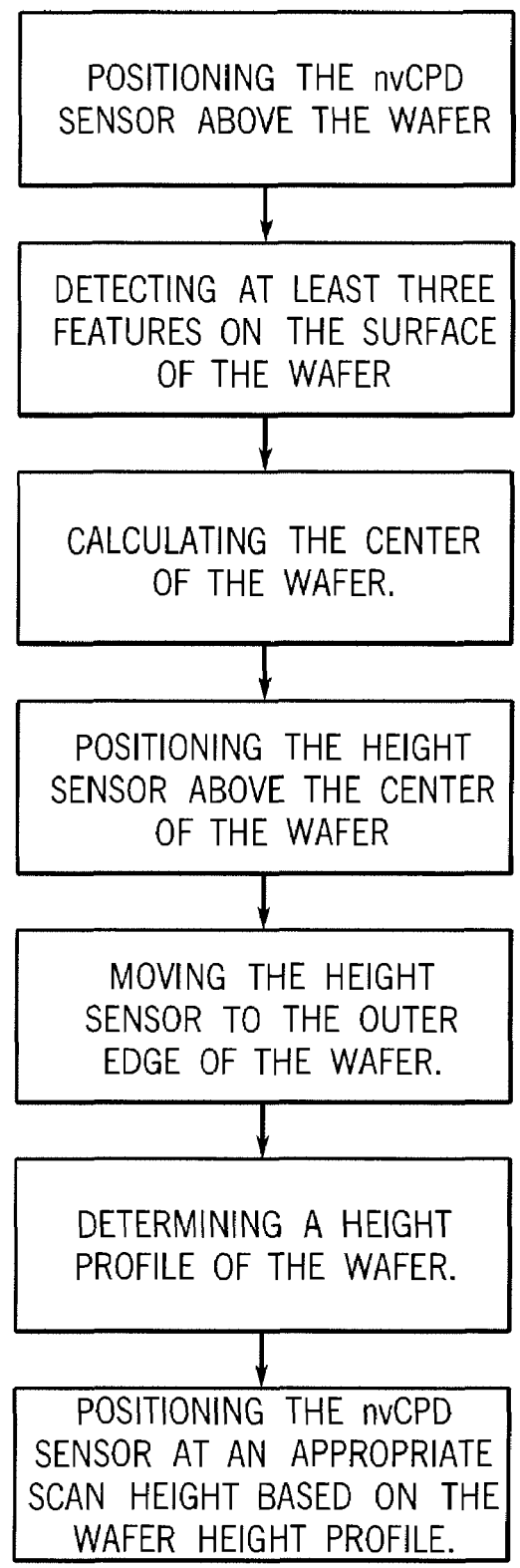
FIG. 18 is a detailed view of the Adjust Starting Position and Height of Probe Above Surface step of FIG. 9.

However, in some embodiments prior to scanning a portion of the wafer, a height profile is established with a height sensor and then the scanning height of the nvCPD sensor is adjusted appropriately. FIG. 18 depicts one embodiment which utilizes a height profile of the wafer to position the sensor. The height profile is determined by first moving the height sensor to the center of rotation and then, with the wafer spinning, the height sensor is moved out toward the edge of the wafer until it senses the edge. Note that this also allows the diameter of the wafer to be determined. The sensor is then moved back toward the center until it is within the wafer flat(s) or notch. One or more height measurements taken along the way establish the profile. An appropriate height for nvCPD sensor scanning is calculated based on the profile, particularly based on the maximum detected height.

As mentioned above, often the nvCPD sensor used in accordance with the principles of the present invention generates a peak signal that behaves like noise. In accordance with the principles of the present invention, denoising algorithms can be applied to both nvCPD signals and nvCPD images. In one embodiment, the nvCPD signal/image data are decomposed into the wavelet domain using one of the wavelets available, such as but not limited to 'Coiflet', 'Daubechies', 'Symmlet', and other such wavelets. Then, as a result of the wavelet decomposition, a series of wavelet coefficients are obtained at a finite number of scales that can be given by the user. A coefficient at a particular scale represents the magnitude of the frequency corresponding to that scale at the point corresponding to that coefficient. The nvCPD signal/image can then be reconstructed by the coefficients in reverse order.

Figure 19:
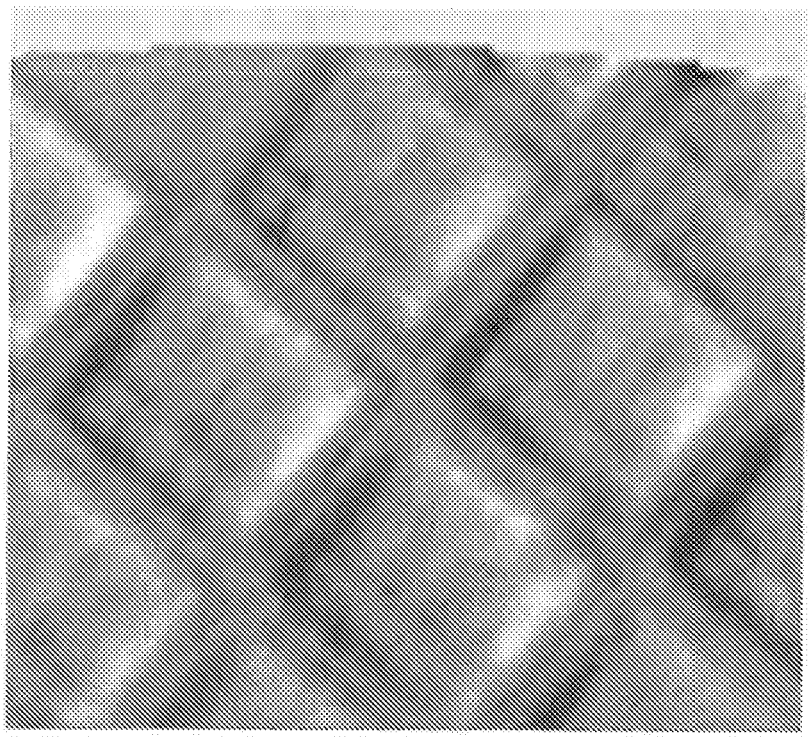
FIG. 19 illustrates nvCPD processed wafer images before deconvolution.
Figure 20:
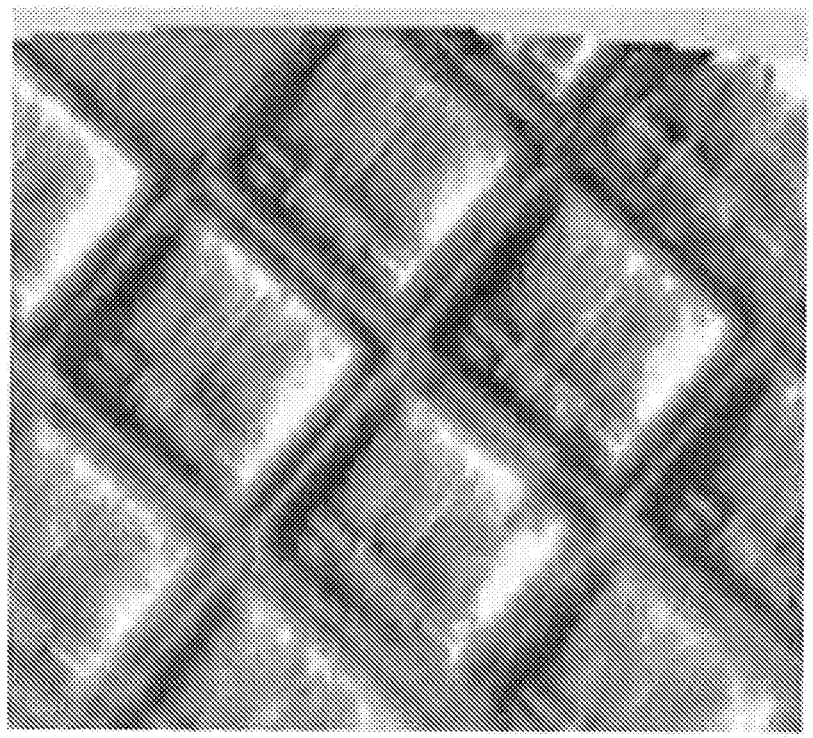
FIG. 20 illustrates nvCPD processed wafer images after deconvolution.

By adjusting the coefficients and performing reconstruction, the three components (peak, low frequency, and noise) of the nvCPD signal/image can be selectively filtered out. To eject the low frequency component from the nvCPD signal/image, only wavelet coefficients at fine scales are used for reconstruction since the low frequency component of the nvCPD signal/image are represented by the coefficients at coarse scales. To eject the noise from the nvCPD signal/image, the coefficients at fine scales can be shrunk softly based on the threshold given. The threshold can be determined using any one of numerous methods known in the art such as, but not limited to, 'Visu', 'SURE', 'Hybrid', 'Min-Max'. The sharp peak signal that is related to contamination on the wafer can be reconstructed substantially in isolation by the wavelet coefficients resulting after performing the two processes above. Thus, noise such as vibrations or a wobbling of the wafer can be filtered out of the signal. FIG. 19 depicts an image produced by a system in accordance with the principles of the present invention without deconvoluting or denoising the data. FIG. 20 illustrates the improved resolution and definition of an image which is denoised in accordance with the principles of the preferred embodiment.

A semiconductor wafer inspection system in accordance with the principles of the present invention which utilizes a nvCPD sensor may, as discussed above, experience a time delay. However, the present invention provides a filtering technique to remove this time delay. First, the time delay circuit is modeled as a first order RC circuit. The continuous-time transfer function of the RC circuit is given by $$\frac{Y(s)}{X(s)} = \frac{1}{\tau s + 1}$$

where X(s) and Y(s) are the Laplace transformation of the input current signal at the probe tip and the output voltage measurement to the data acquisition, and $\tau$ is the time delay constant.

The continuous current signal is fed into and amplified by the amplifier, and then converted into a discrete signal through the A/D converter. In this way, the collected data by the computer at the final stage is a series of discrete data. For digital signal processing, the continuous-time transfer function of the RC circuit is converted into a discrete-time transfer function based on Z-transformation. This discretized transfer function has the form $$\frac{Y(z)}{X(z)} = \frac{\alpha}{z + \beta}$$

wherein the constants $\alpha$ and $\beta$ are determined by the discretization method employed, the sampling time and the time delay constant, $\tau$.

Next, in a preferred embodiment, the impulse response of the discretized transfer function is determined. In general, the impulse response is a finite number of positive discrete values that converges to zero gradually. Once the impulse response is found, the deconvolution process with the impulse response is performed on each track data separately.

Figure 16:
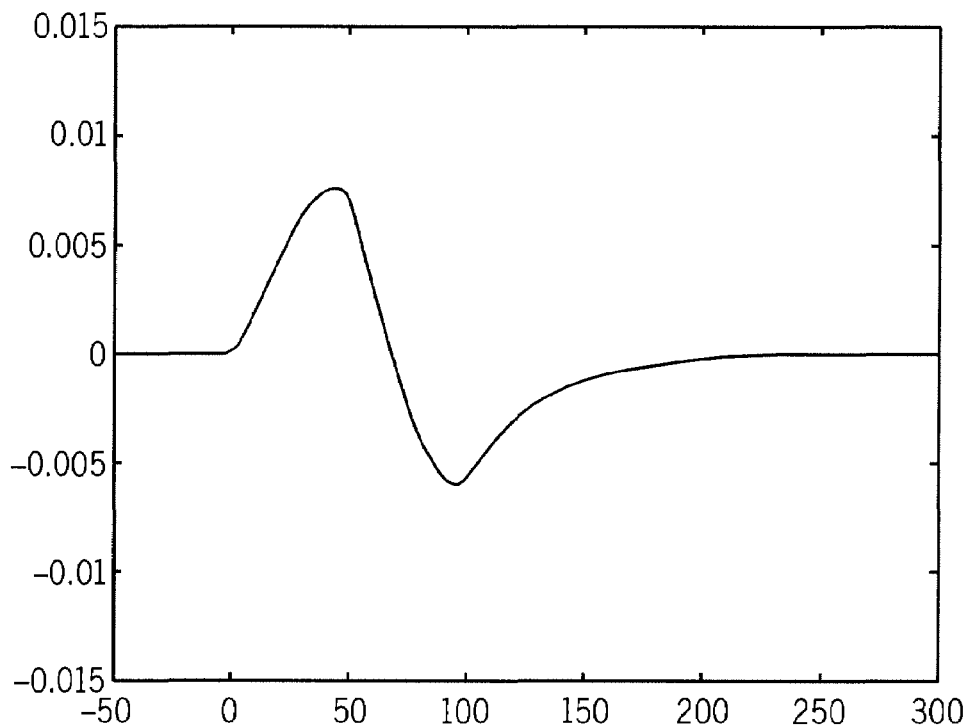
FIG. 16 illustrates a chart depicting a typical nvCPD signal where there is a set of peaks comprising a positive peak and a negative peak having non-equivalent heights.
Figure 17:
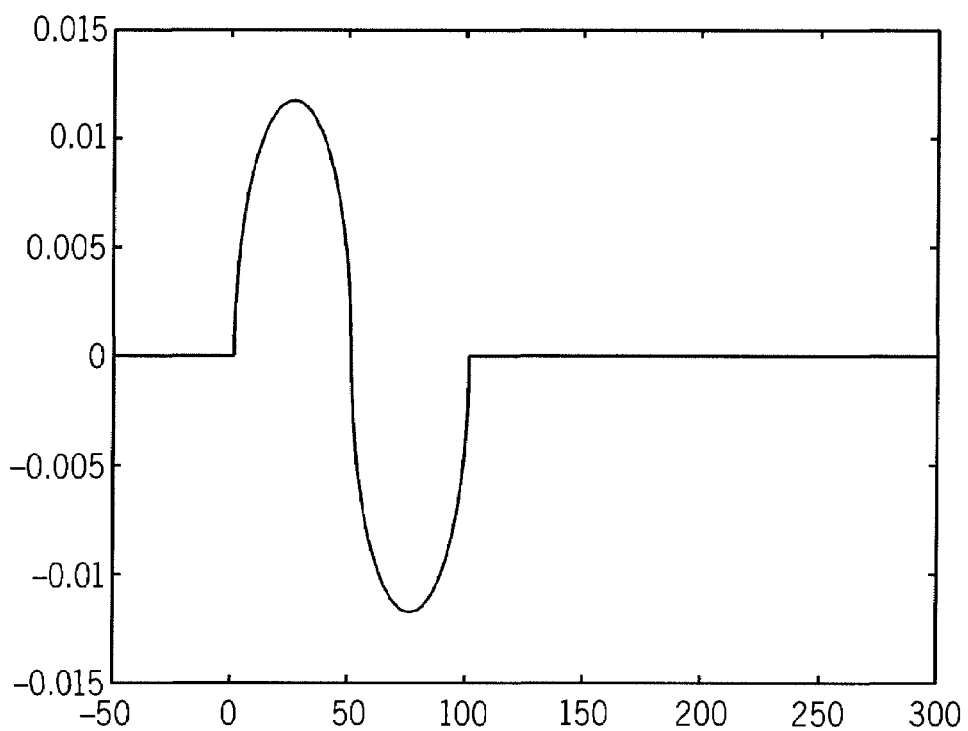
FIG. 17 illustrates a chart depicting a signal output of one embodiment of the present invention where the positive peak height is substantially equivalent to the negative peak height.

Time constant prediction is important and can be assessed by comparing the positive peak height and the negative peak height. FIG. 16 shows a typical nvCPD signal where there is a pair of a positive peak and a negative peak. It is shown that the positive peak is higher than the negative peak. With zero time delay, the signal would look like FIG. 17, where the positive peak height is equivalent to the negative peak height.

By comparing the positive peak height with negative peak height, the time constant can be estimated correctly. If the time constant is underestimated, the former peak (in this example, the positive peak) is higher than the latter peak (in this example, the negative peak). If the time constant is overestimated, the former peak is lower than the latter peak. By varying the time constant, a point when the positive and negative peaks are equivalent in height could be found to predict the time constant correctly.

In one exemplary embodiment, the present invention provides a method and apparatus to allow for the isolation of the topographical information by filtering out the chemical information from the sensor apparatus. This embodiment utilizes a direct current (D.C.) bias applied to the system. In one exemplary embodiment, the bias is applied to the sensor. In another exemplary embodiment, a similar bias is applied to the sample surface directly instead of to the sensor. A first scan of the sample surface is taken with a negative bias applied to either the sample or the probe and the data is recorded. A second scan of the wafer is taken with a positive bias applied to which ever of the probe or the probe had the bias applied during the first scan. One of ordinary skill in the art will appreciate that this order could be reversed and the positive bias scan could be done first followed by a negative bias scan. The signal with the negative bias applied is then subtracted from the signal with the positive bias leaving a signal related only to geometric change on the sample surface.

Figure 24A:
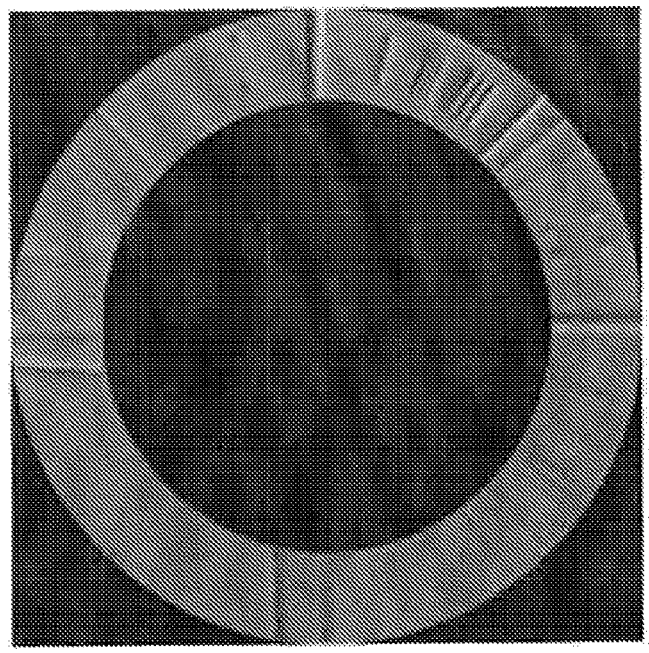
FIG. 24A shows an image of a semiconductor wafer generated by an apparatus of the present invention with no bias voltage.
Figure 24B:
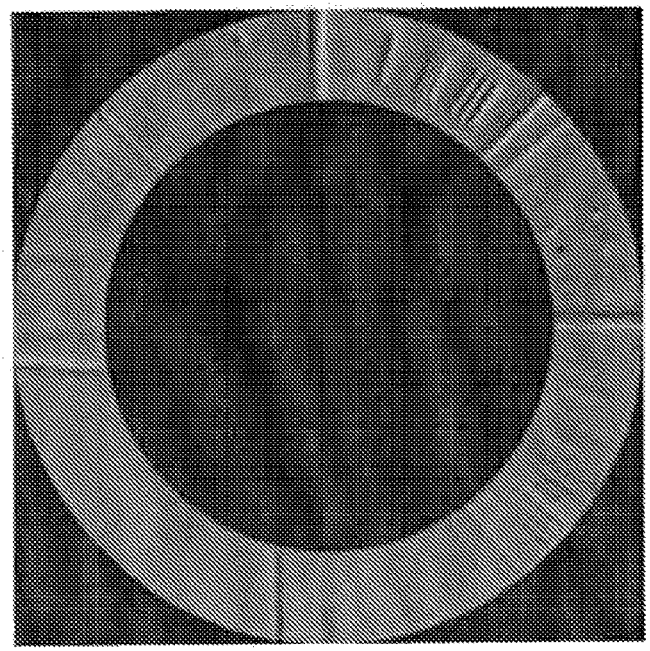
FIG. 24B shows the image of the same semiconductor wafer where a 9 volt bias is applied.
Figure 24C:
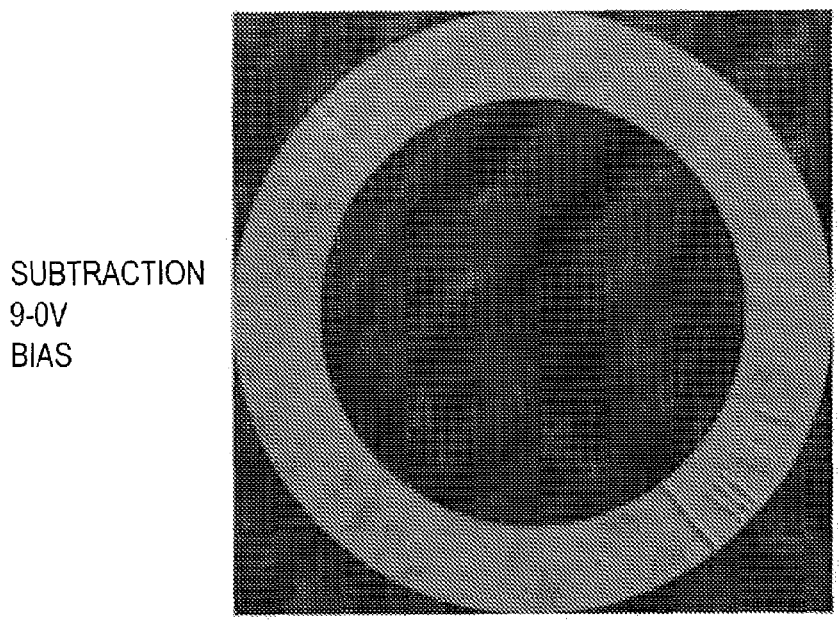
FIG. 24C shows the image generated by an apparatus of the present invention, where the bias signal has been eliminated as shown mathematically below.
Figure 24D:
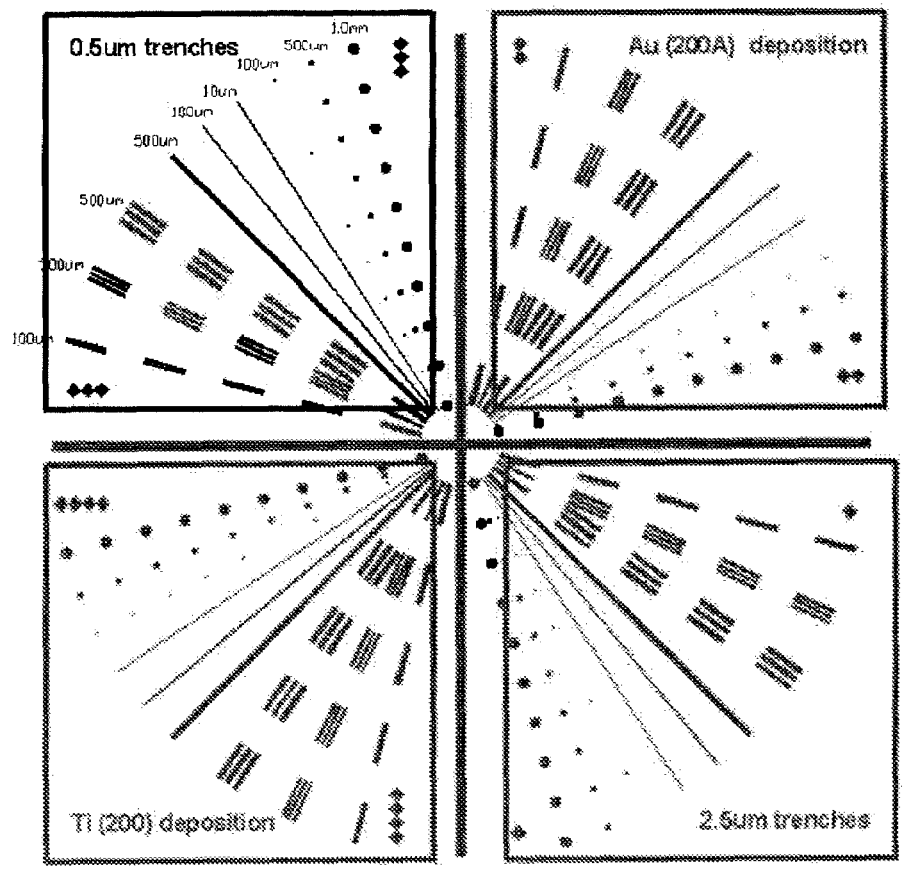
FIG. 24D illustrates the composition of the semiconductor wafer inspected in FIGS. 24A-C.

FIGS. 24A-D illustrate the images of a wafer at each of the various steps. FIG. 24A shows an image of a semiconductor wafer generated by an apparatus of the present invention with no bias voltage. FIG. 24B shows the image of the same semiconductor wafer where a 9 volt bias is applied. FIG. 24C shows the image generated by an apparatus of the present invention, where the bias signal has been eliminated as shown mathematically below. FIG. 24D illustrates the composition of the semiconductor wafer inspected in FIGS. 24A-C. As can be seen, the geometrical or topographical features were strengthened while the chemical features were weakened. The basic equations relating to nvCPD inspection can be used to illustrate this embodiment.

As previously stated, the basic CPD equation is:

$$i = C\frac{dV}{dt} + (\phi_P - \phi_S)\frac{dC}{dt}$$

The equation with positive bias applied is:

$$i_{+Bias} = C\frac{dV}{dt} + (\phi_P - \phi_S + V_{Bias})\frac{dC}{dt}$$

The equation with negative bias applied is:

$$i_{-Bias} = C\frac{dV}{dt} + (\phi_P - \phi_S - V_{Bias})\frac{dC}{dt}$$

Thus, by subtracting the signal with a negative bias from the signal with a positive bias, the result is:

$$i^* = i_{+bias} - i_{-bias} = 2V_{Bias}\frac{dC}{dt}$$

Solving the difference shows the signal dependent on only geometry changes of surface (represented by capacitance):

$$i^* = 2V_{Bias}\frac{dC}{dt}$$

In an exemplary embodiment, the present invention relates to a method and apparatus to allow for the preservation of signal to noise ratio and for providing a substantially uniform data density by varying the rotational speed to provide substantially uniform linear speed of the sample relative to the probe. A variable speed chuck is provided which decreases the rotational velocity in proportion with the motion of the probe to provide the probe with substantially even data exposure. Thus, the chuck is able to compensate for the increasing data per revolution by reducing the revolutions per minute to maintain a substantially even data density.

In an exemplary embodiment, the system of the present invention includes a plurality of probes. The tips of each of the plurality or probes may be arranged in a variety of different arrangements known in the art, including but not limited to linear arrays and two-dimensional arrays. It has been shown that multiple probe tips in a variety of configurations, as just discussed, provide the system of the present invention with a decrease in the time required to scan a sample surface. The decrease in speed is inversely proportional to the percentage increase in the number of probes used. The individual probes in the plurality have, in one exemplary embodiment, varying characteristics. Such characteristics may include, but are not limited to, bias voltage and height. It is believed that the use of a plurality of probes provides, in addition to a decreased inspection time, an improvement in lateral resolution and chemical sensitivity. Such an improvement in lateral resolution and chemical sensitivity may be accomplished, in one embodiment, by the use of differentially comparing the separate probe data streams such as by a combination of separate voltage tracks.

In another exemplary embodiment, a method is provided for calibrating the height of the probe tip. This procedure assumes that the height sensor and nvCPD sensor are rigidly mounted with respect to each other, and that the relative height of the sensors (z) can be precisely determined. In our system, the height sensor and nvCPD sensor are mounted to the same metal fixture, and their relative height is determined by reading the z-axis encoder on the positioning system.

In one exemplary embodiment illustrated in FIGS. 25A-E, the present invention includes a calibration process for calibrating the height of the nvCPD sensor. As shown in FIG. 25B, the height sensor is positioned above a reference surface so that the distance between the reference surface and the height sensor is within the range of detection for the height sensor. The height of the sensors is recorded as z1. The height sensor reading is recorded as h1. As shown in FIG. 25C, the nvCPD sensor is moved slowly down while the level of the nvCPD signal is monitored. When the nvCPD sensor probe tip contacts the reference surface, then the output of the nvCPD sensor experiences a significant change. This is automatically detected by the scanning system, and the downward motion stops. The height is recorded as z2. The nvCPD sensor probe tip can now be positioned at a desired height above any surface. This is accomplished as follows. As shown in FIG. 25D, if the desired height is h*, then the height sensor is positioned above the surface so that the surface is within the measurement range of the height sensor. The height is recorded as z3 and the height sensor reading is recorded as h3. As shown in FIG. 25E, the nvCPD sensor is then positioned above the same point and the height adjusted to z*=z3-(h3-h1)-(z1-z2)+h*, which results in a height of the nvCPD sensor probe tip above the surface of h*.

Although the present invention has been frequently described in relation to the scanning of a semiconductor wafer which is spun relative to a probe which takes circumferential tracks of data, one skilled in the art would appreciate that the present invention is not limited to such. For example, the present invention may, in one exemplary embodiment, be used to scan liquid crystal display panels, which are generally too bulky to be spun. In this embodiment, the probes are raster-scanned across the sample surface. In addition, in another exemplary embodiment, the probe may be held stationary and the sample surface moved relative thereto. In yet another exemplary embodiment, the sample surface may be held stationary and the probe may be moved relative thereto.

Figure 26A:
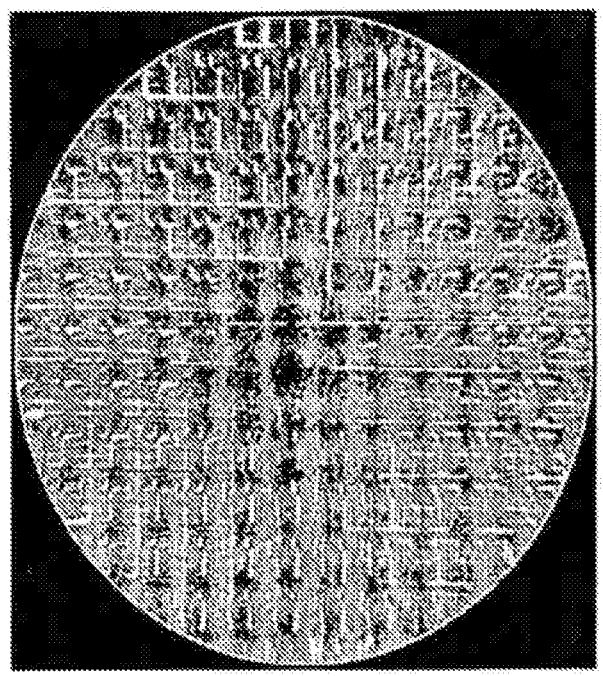
FIG. 26A shows a typical full wafer nvCPD scan of a 200 mm Cu CMP wafer which has been processed in a two step CMP approach.
Figure 26B:
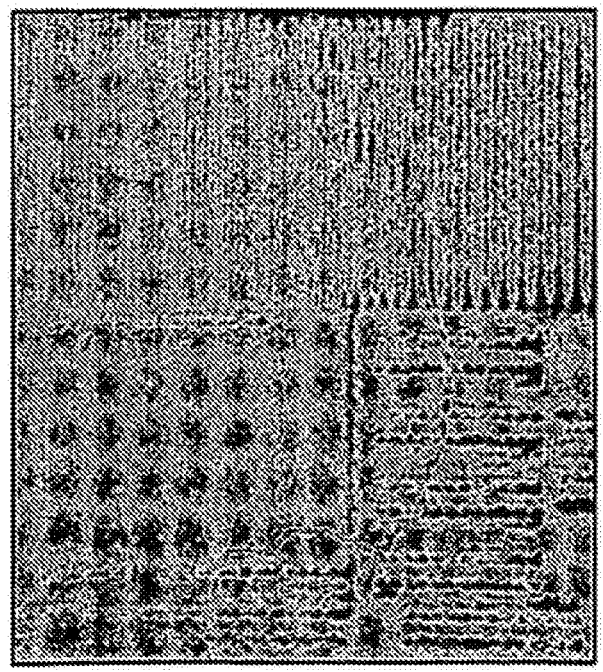
FIG. 26B shows work function imaging of a full 200 mm post Cu CMP process wafer with Sematech 831AZ pattern with a zoom-in section which indicates the work function variation on Cu and dielectric surface inside a die after CMP processing.

In addition to a system using a nvCPD sensor to collect the relative CPD data, in an exemplary group of embodiments, the present invention also utilizes a vibrating CPD sensor, as discussed above, to collect absolute CPD data. The system of the present invention may utilize a single sensor capable of operating in a nvCPD mode or vCPD mode, or in another embodiment separate nvCPD and vCPD sensors may be provided. FIGS. 26A-B show a typical full wafer nvCPD scan of a 200 mm Cu CMP wafer which has been processed in a two step differentiated approach described above. The image contains over 10 million data points, and can be manipulated to examine an enlarged area of interest. FIG. 26B shows a sample area of interest that consists of a single die.

One exemplary system of the present invention includes a spindle and a 3-axis linear motion system. The CPD sensor (having a nvCPD and vCPD mode) and the scan height sensor are mounted on the linear motion stages. A semiconductor wafer is mounted on a vacuum chuck attached to the spindle. The wafer is spun and a height sensor is used to measure the wafer height and adjust the gap between the CPD sensor probe tip and the wafer surface. The linear motion system positions the nvCPD sensor (CPD sensor in nvCPD mode) above the wafer surface, and concentric, circular tracks of data are acquired as the sensor is stepped from the outer edge of the wafer to its center of rotation. The data is collected and stored in a computer, and then processed with imaging software to generate wafer images and quantitative data on wafer non-uniformity.

The CPD measurement system of the present invention includes various modes. In an exemplary embodiment, the system supports operation in multiple modes of operation. The operational modes may be used alone or in combination to derive the desired information from a sample.

In one embodiment, a calibration mode is performed to ensure the accuracy of the system of the present invention. Calibration is required to determine the work function of the probe tip, or changes in the work function of the probe tip. This is accomplished by making a vibrating CPD measurement on a surface of known work function. In an exemplary embodiment, this surface is a non-reactive metal placed within the workspace of the scanning system. In one embodiment, the calibration is performed prior to one of the testing modes described below. In an alternative embodiment, periodic checks of the probe tip work function are performed as part of a self-check mechanism.

The system of the present invention may comprise more than one mode for testing a sample to determine the presence or absence of defects. In a manual mode, the sample is scanned using the non-vibrating, differential CPD measurement mode. The user is then presented with an image of the wafer surface, and selects a point or series of points for vibrating CPD measurement. In one embodiment, these points are "predetermined" and each sample is tested via the vCPD probe at the same set of points. The system automatically moves to each location and measures the absolute CPD. In an exemplary embodiment, the results are presented graphically to the user and can be stored in a results file. This mode is useful for interactive studies of wafer surface CPD, and would be necessary to determine whether CPD values at particular points are useful for specific inspection tasks.

In another embodiment, an automated taught-point mode is provided. In the automated taught-point mode, the user defines one or more points on the surface of the wafer for vibrating CPD measurement (using manual mode), and associates these points with an inspection strategy or recipe. During the inspection process, the system automatically positions the sensor at the taught positions and makes vibrating CPD measurements. The data is included in the results. In an exemplary embodiment, this data is used for process control and determining Pass/Fail conditions for inline semiconductor wafer manufacturing processes.

In yet another embodiment, an automated defect classification mode is provided. In this mode, the sample is imaged using the non-vibrating CPD scanning mode, and defects are automatically detected as previously discussed using a nvCPD sensor alone via changes in the differential CPD data. The system then automatically determines the location of these defects and makes vCPD measurements at one or more of these locations to determine their absolute CPD. This information can be useful in classifying the type of defect.

In yet another embodiment, a manual vibrating CPD measurement mode is provided. A vibrating CPD measurement is divided into the following steps: (1) position the sensor in X and Y, (2) position the sensor in Z, (3) make a measurement. The sensor is positioned at the center of rotation and at a known height above the sample surface. The sample is rotated so that the flat is in the desired position, and a vacuum is applied then removed. Once the sample is placed on the chuck, a vacuum is applied, the flat is positioned, and the CPD sensor is moved to the center of rotation a known height above the sample (typically 100 microns). At this point the system is ready to begin vibrating CPD measurement. The sensor is positioned at a known X and Y location relative to the center of rotation. At this point the sensor has been positioned in X and Y.

In one embodiment, a PZT controller is utilized with software to control and monitor the vCPD probe. For example, for a 500 micron diameter probe, the following parameters are set:
  Sample Rate: 100000
  Scan Length: 10000
  Bias: 6
  Coupling: AC
  Frequency Filtering: Enabled
  Stat: Std Dev Continuous acquisition is initiated. The following additional parameters are set.
  Bias Change Delay: 1020
  Amplitude: 2
  Frequency: 490
  Bias Voltages: −5, −3, 3, 5

Vibration of the probe tip is initiated. The probe is lowered towards the wafer surface. In an exemplary embodiment, the standard deviation value is monitored while the probe tip is manually lowered towards the wafer surface using the software. When the standard deviation exceeds 0.005 V then sensor motion using the software is halted. The manual offset of the PZT controller is then used to slowly lower the probe tip towards the wafer surface while the standard deviation is monitored. The sensor probe tip is lowered until the standard deviation is 0.010 V.

Vibration is stopped. At this point the sensor is positioned in Z. The following acquisition parameters are set:
  Bias: 0
  Scan Length: 50000
  Stat: Freq Domain A vibrating CPD measurement is initiated. The signal magnitude is automatically measured at the defined bias voltages (four different voltages in this exemplary embodiment), a line is fit to this data, and the zero crossing of the line is calculated. This zero crossing is the CPD value at that point. In one embodiment, this value is graphically displayed to the user. This completes the measurement and the probe can now be raised and moved to a new location. Achieving highly repeatable CPD measurements depends on controlling many factors that can affect measurement results. Some of these are listed briefly below.

1) Mechanical Vibrations. Vibration isolation may be desirable to reduce mechanical vibrations that can affect results.
2) Surface Charging. Static charge on the surface of the wafer can affect measurements, and should be controlled using an ionizer or other static control device.
3) Temperature and Humidity. These may affect measurements and should be controlled.
4) Vibration magnitude. It is important to control the magnitude of vibration and this should be monitored using sensor feedback.
5) Measurement Height. The measurement height should be controlled as variations can affect measurement results.

Figure 35:
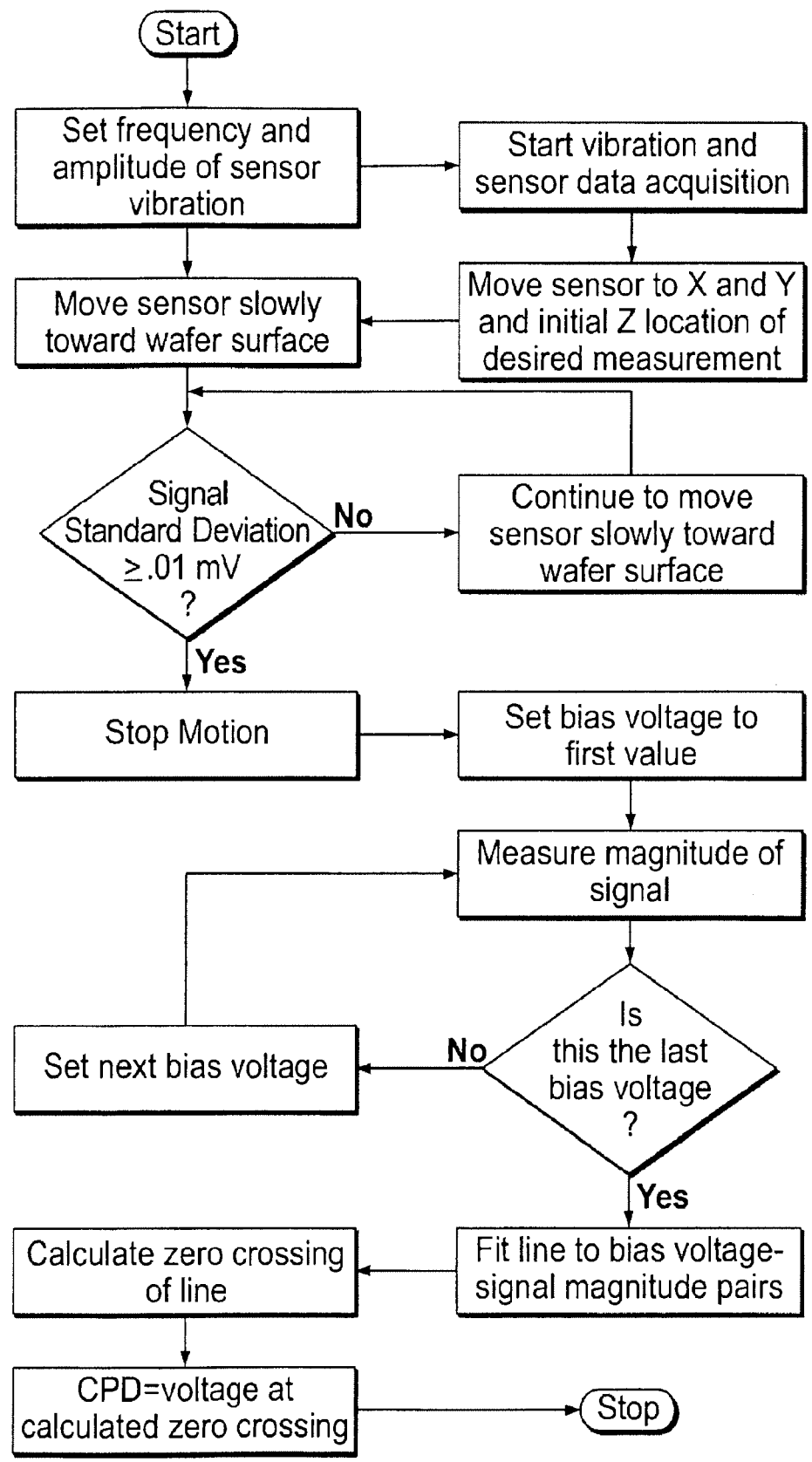
FIG. 35 is a flowchart depicting the steps during automatic vCPD measurement.

It should be appreciated that in a preferred embodiment, the previously described manual steps of taking measurements can be performed automatically. FIG. 35 illustrates the steps necessary in an automated measurement process.

The following non-limiting example describes methods of preparation of test wafers and sensing characteristic images for identifying certain defect states, chemical states, electrostatic states and mechanical features present on a semiconductor wafer surface.

EXAMPLE 1

Sample wafers can be created by dip coating the wafer 15 in solutions that contain known concentrations of contaminants. Part of this example describes metal contaminants such as Cu and Fe, although any manner of chemical contaminants can be evaluated in this way. The wafer 15 described is either a 100 mm or 150 mm wafer, although these examples apply to any size wafer. The wafer surface 16 is prepared by dipping in HF to remove oxides. The wafer 15 is then cleaned and partially dipped in the metal contaminant solution. The amount of solution remaining on the wafer 15, and the resulting concentration of contaminant on the wafer surface 16, is controlled by selecting dip coating parameters such as the extraction rate.

Partial dipping of the test wafer 15 is preferred to create a transition from clean to contaminated areas. Because the nvCPD signal is differential, the nvCPD sensor 12 detects changes on the wafer surface 16, as opposed to an absolute value relating to surface condition. This aspect of nvCPD sensors 12 is offset by the ability to rapidly image and detect localized contamination anywhere on the surface of the wafer 15.

Figure 7:
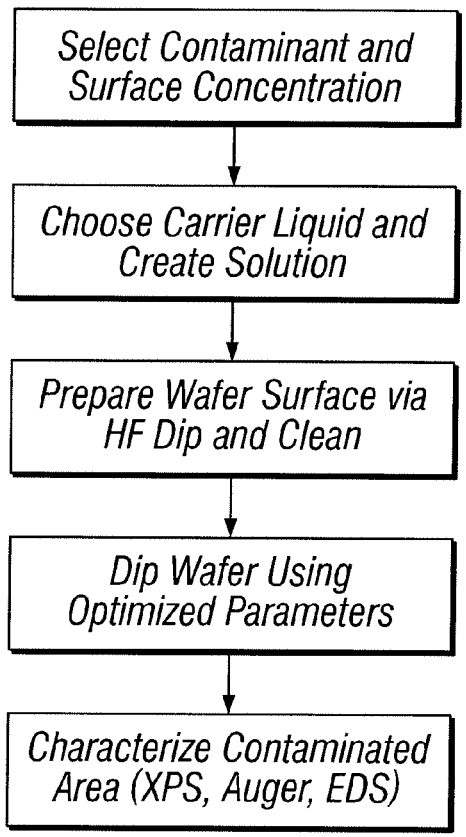
FIG. 7 illustrates steps for creating test wafers which are partially coated with known concentrations of contaminants.

After preparation, each test wafer 15 can be, if necessary, analyzed using an appropriate combination of XPS, Auger, and RBS (or other well known surface analysis methods) techniques to measure actual contaminant concentrations in the dipped areas of the wafer 15. Each step involved in the sample wafer preparation process is shown in FIG. 7. In a production line methodology, standards can be established correlating measure actual contamination concentration to nvCPD data for routine use.

After each sample wafer 15 is created, it can be imaged using a radially scanning nvCPD imaging system 10 constructed in accordance with the invention. As described before, FIGS. 8A and 8B show basic forms of the nvCPD imaging system 10, and FIG. 9 shows another flow diagram illustration of wafer processing. The system 10 employs the nvCPD sensor 12 mounted on the previously described three-axis positioning system 26. This positioning system 26 is used to position the nvCPD sensor 12 above the wafer surface 16 to be imaged, and to scan the nvCPD sensor 12 radially across the wafer surface. The wafer 15 is mounted on a spindle that rotates at high speed (1800 rpm) beneath the nvCPD sensor 12. The system 10 operates by acquiring multiple consecutive tracks of data as the nvCPD sensor 12 is stepped along the radius of rotation of the wafer 15.

Figure 10A:
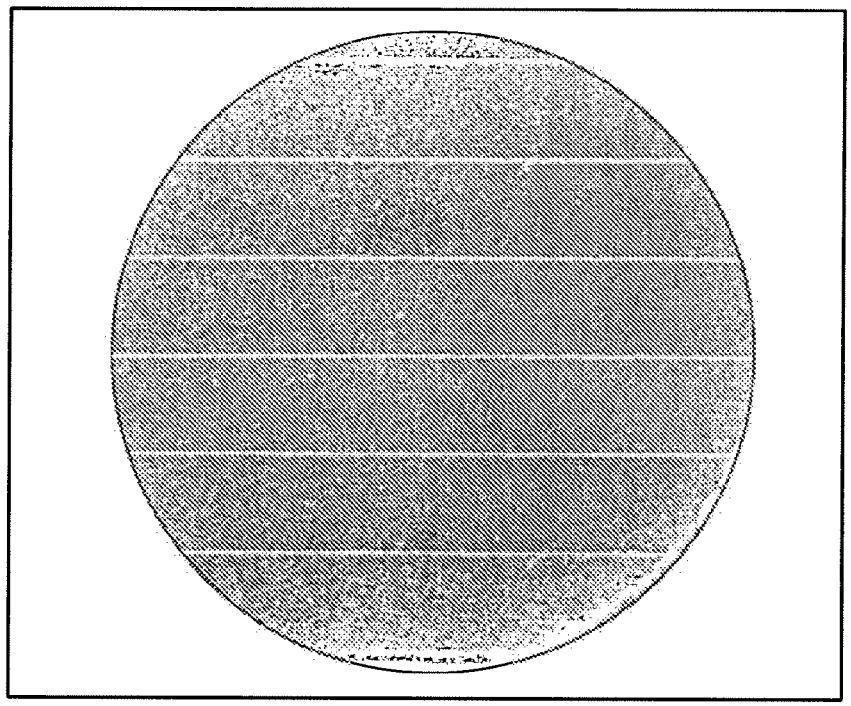
FIG. 10A illustrates an optical image of a 100 mm diameter silicon wafer after application of a vacuum pick-up device.
Figure 10B:
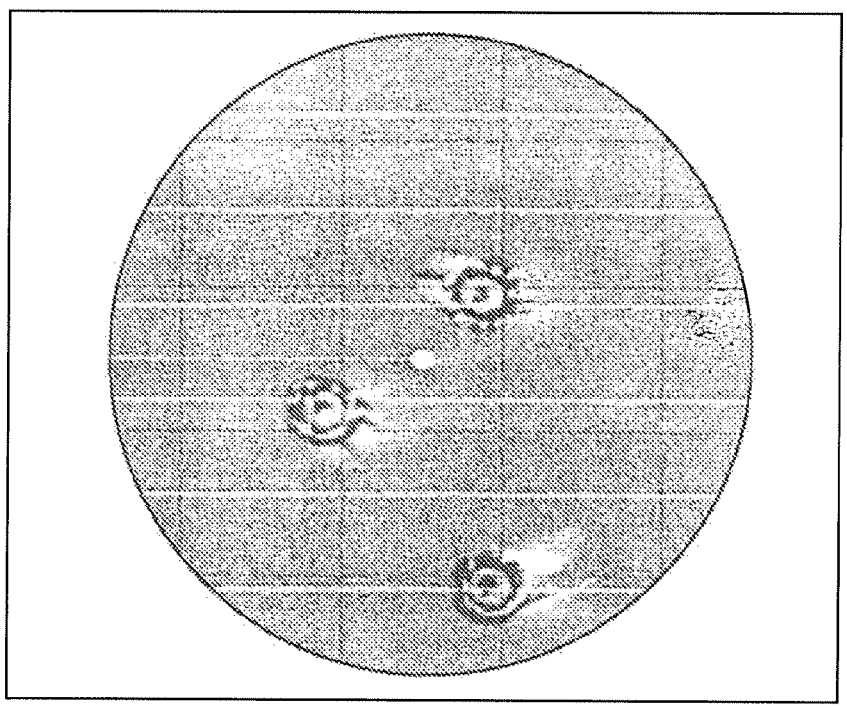
FIG. 10B illustrates an nvCPD image of the wafer of FIG. 10A.

The imaging system 10 has been used for a variety of surface analysis experiments. FIGS. 10A, 10B, 11A, and 11B show sample wafer images that were generated using the nvCPD sensor 12 imaging for wafer inspection. The images show optical images in FIGS. 10A and 11A and nvCPD images in FIGS. 10B and 11B of a 100 mm form of the wafers 15. The first wafer 15 was cleaned, and then a small vacuum pick-up device was attached to the surface of the wafer 15 in three locations. The optical image of FIG. 10A shows no evidence of any change on the surface 16 of the wafer 15. The nvCPD image of FIG. 10B shows a very large signal at the locations where the pick-up device was applied. The nvCPD signal is believed to be the result of a small amount of residue left on the surface 16 by the pick-up device.

Figure 11A:
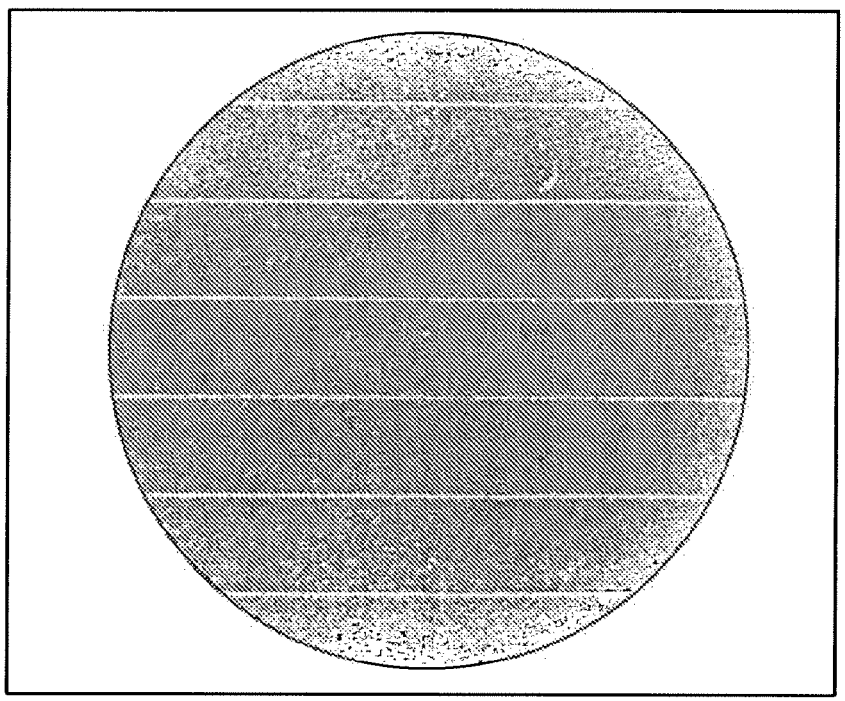
FIG. 11A illustrates an optical image of a second silicon wafer after applying alcohol while spinning the wafer and allowing the alcohol to dry.
Figure 11B:
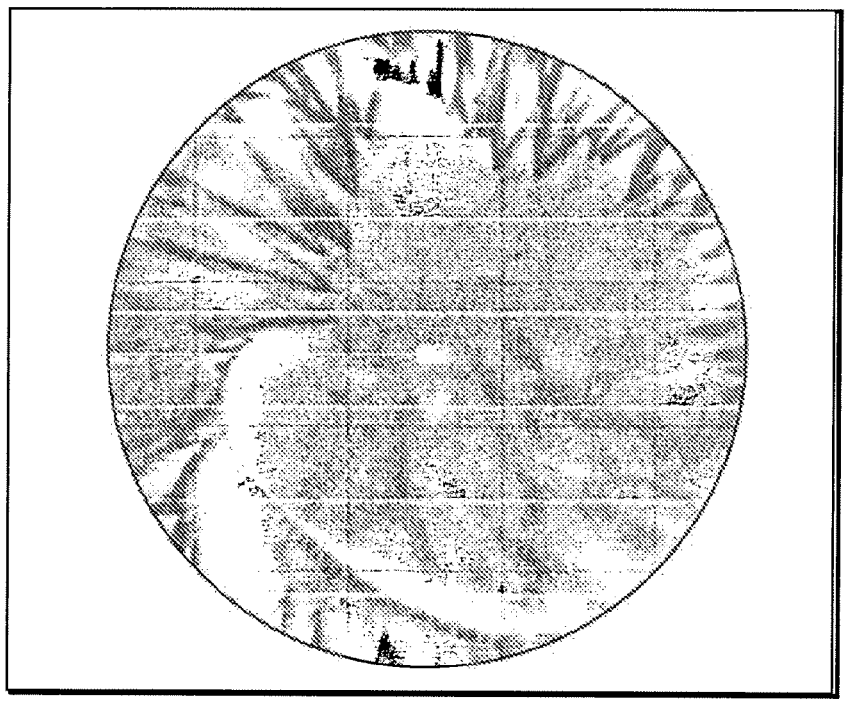
FIG. 11B is an nvCPD image of the same wafer of FIG. 11A.

The second set of images in FIGS. 11A and 11B show a wafer 15 that has had alcohol spun-on and then dried. The resulting residue is not visible in the optical image, FIG. 11A, but is clearly visible in the nvCPD image, FIG. 11B. These images provide a clear demonstration of the usefulness of nvCPD sensor 12 for wafer inspection. Through careful measure of a full range of defect states and chemical constituents it is possible to correlate an image with a particular chemical state, defect, or combination thereof.

Figure 12A:
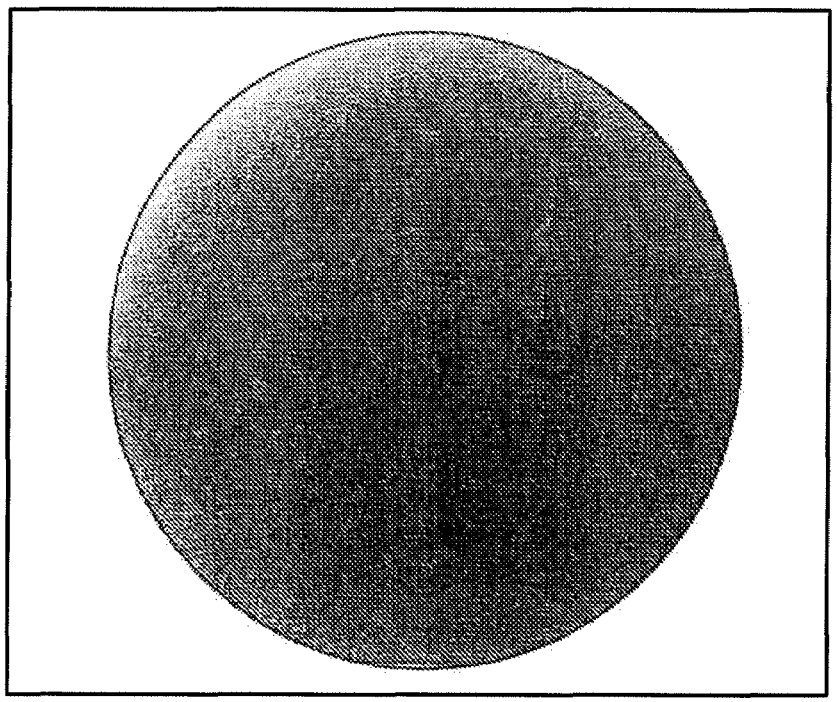
FIG. 12A illustrates an optical image of a silicon wafer after application of a latex glove mark.
Figure 12B:
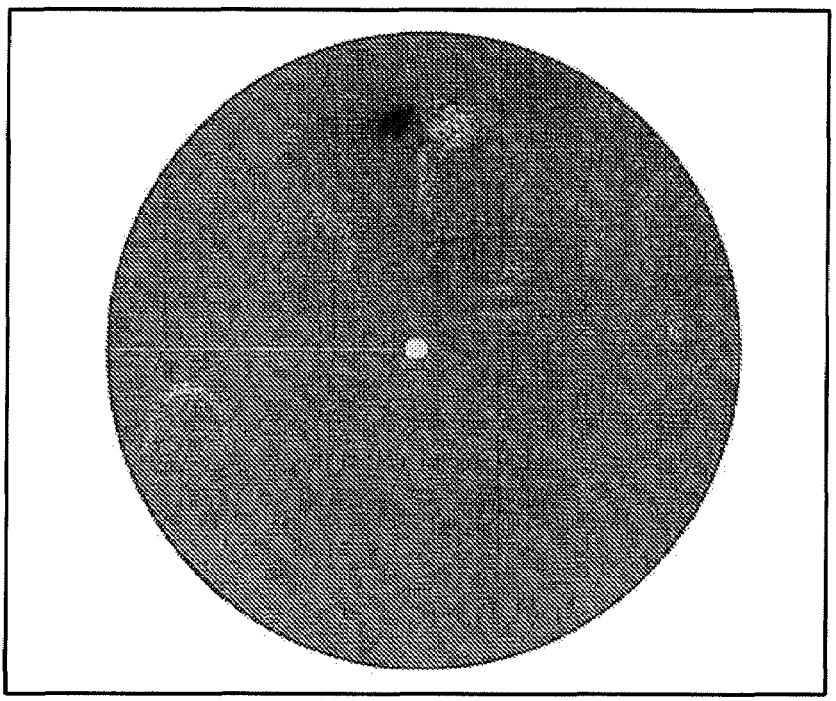
FIG. 12B is an nvCPD image of the same wafer of FIG. 12A.
Figure 13A:
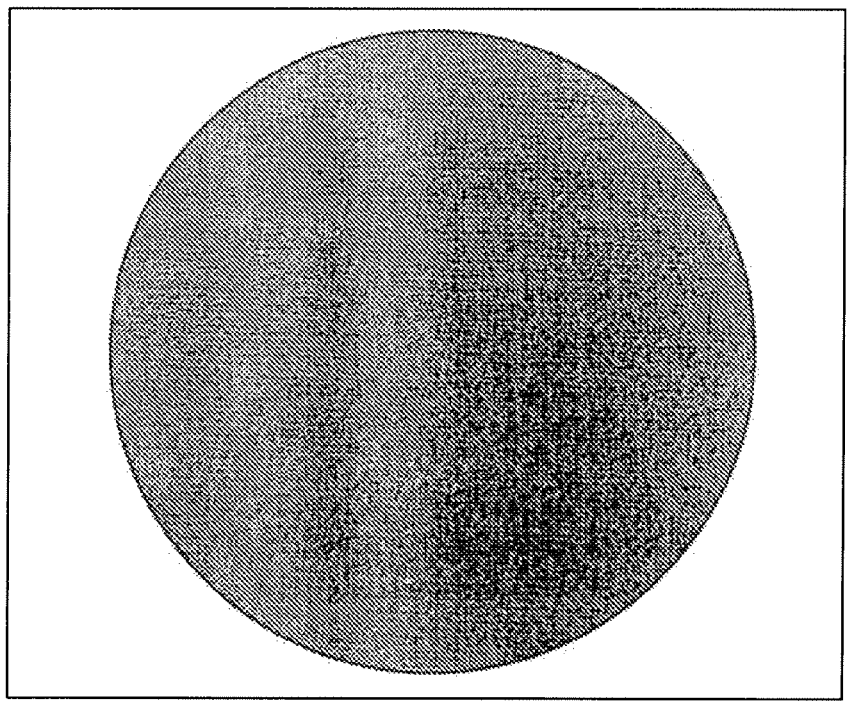
FIG. 13A illustrates an optical image of a silicon wafer having human fingerprints on the wafer.
Figure 13B:
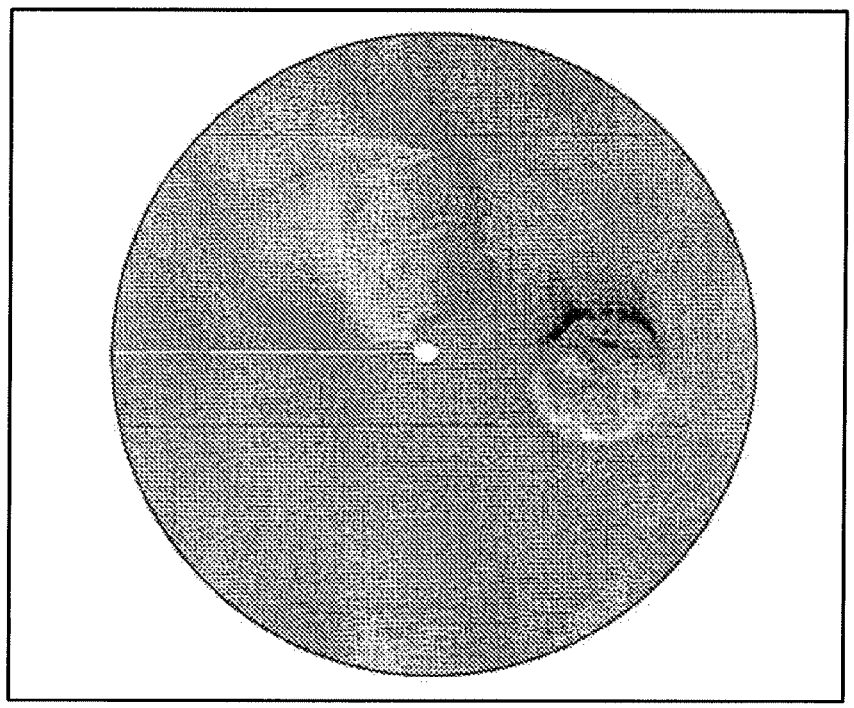
FIG. 13B illustrates an nvCPD image of the wafer of FIG. 13A.
Figure 14:
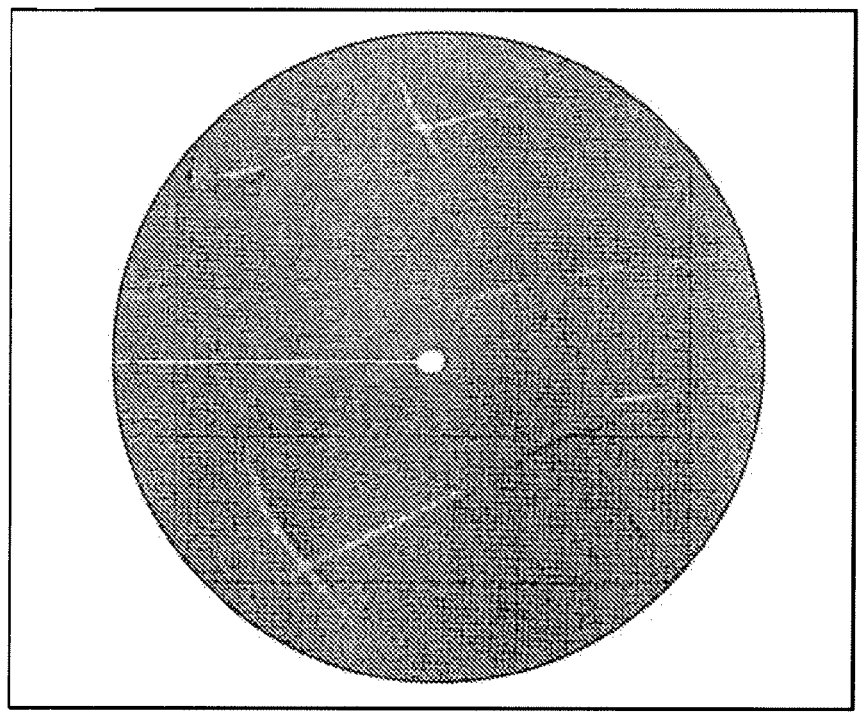
FIG. 14 illustrates an nvCPD image of a silicon wafer after brushing the wafer surface with a stainless steel tool.
Figure 15:
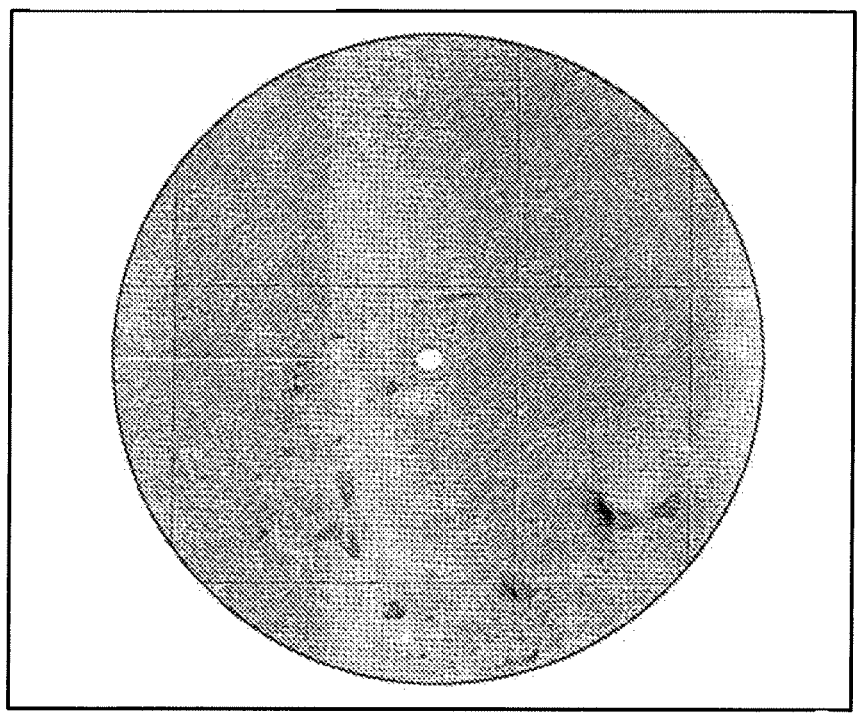
FIG. 15 illustrates an nvCPD image of a silicon wafer after pressing an aluminum fixture onto the wafer surface.

FIGS. 12A and 12B show, respectively, an optical image of latex glove marks and a nvCPD image of latex glove marks. FIGS. 13A and 13B show, respectively, an optical image of human fingerprints and an nvCPD image of the fingerprints. FIG. 14 shows a nvCPD image of a wafer 15 after brushing the wafer 15 with a stainless steel tool, and FIG. 15 shows a nvCPD image of the wafer 15 after pressing an aluminum fixture onto the wafer surface 16. All these example images were acquired using the nvCPD sensor 12 with the probe sensor tip 14 having a diameter of approximately 60 microns measured over a period of approximately 30 seconds.

EXAMPLE 2

Figure 33:
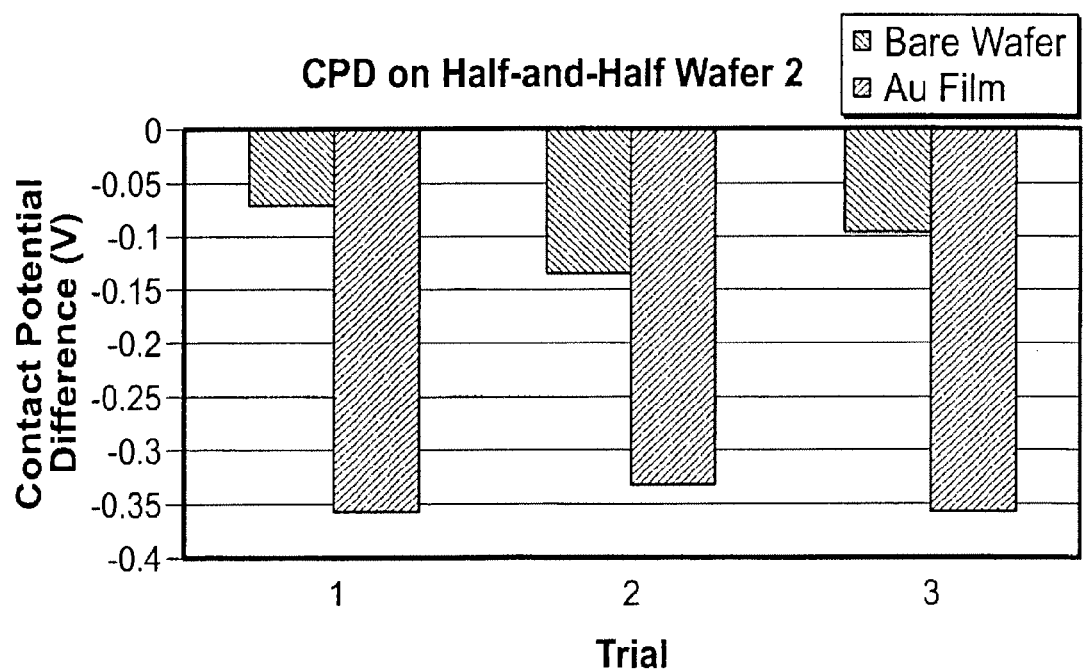
FIG. 33 is a graphical representation of the CPD data for each of the trials.
Figure 32A:
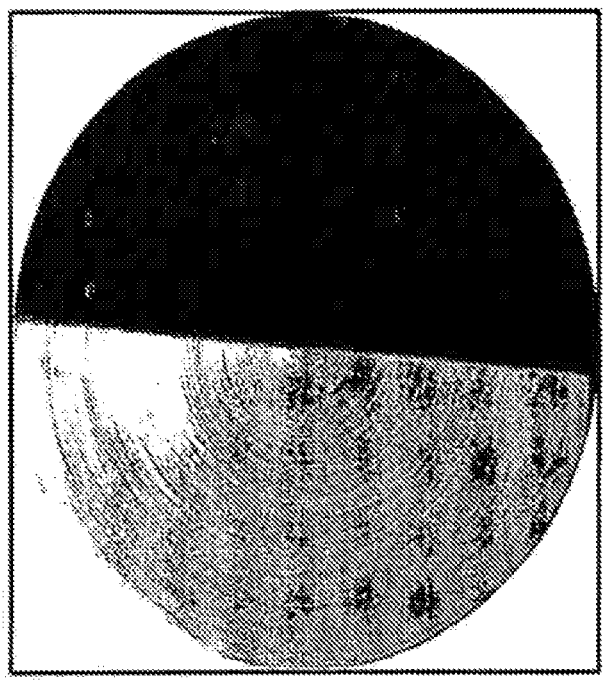
FIG. 32A shows the nvCPD scanned image of the 100 mm wafer with half of the surface coated with a gold film.
Figure 32B:
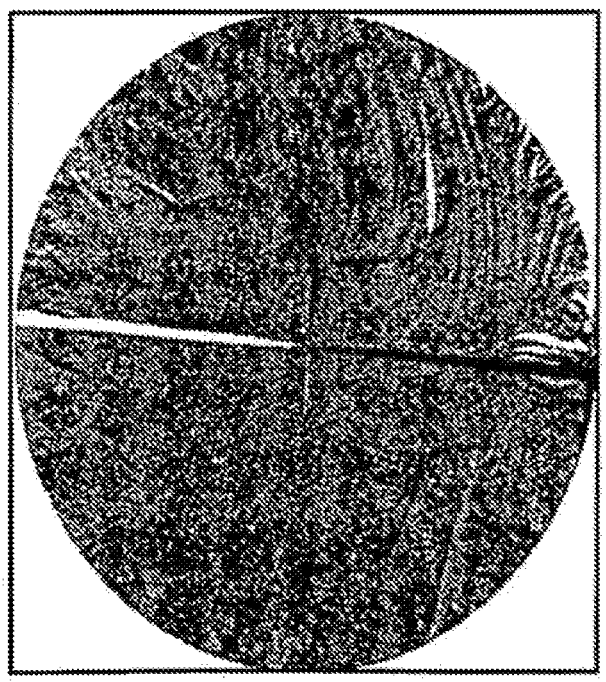
FIG. 32B illustrates the same image with the data integrated.
Figures 34A, 34B:
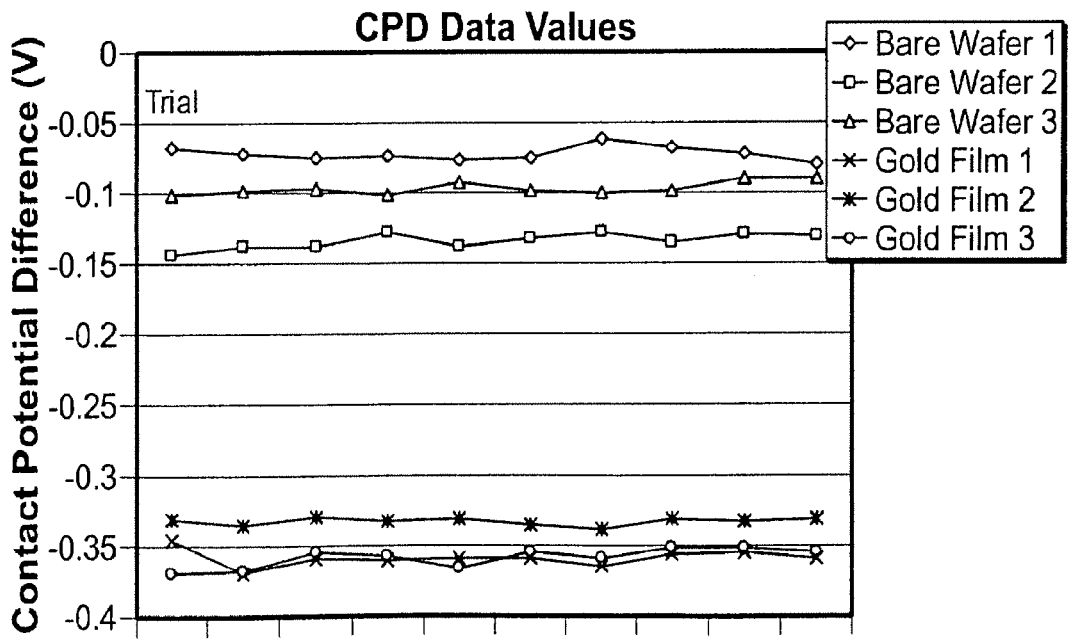
FIG. 34A illustrates the precision of the present invention, showing the data for each of the ten measurements in each of the three separate trials.
FIG. 34B illustrates the data of FIG. 34A in graphical form.

Measurements were made at six (6) locations on one hundred (100) millimeter wafer. The surface of the wafer was coated with gold on a first half. The second half was left uncoated, i.e. in its "natural", bare silicon state. Three trials were performed on the bare silicon surface and the gold film surface. The probe—made from 500 micron diameter copper wire—was vibrated at 490 Hz, with a vibration amplitude of a few microns peak-to-peak. In addition, an ionizer was utilized to reduce the effect of surface charging. Ten measurements were made at each location. As can be seen in FIG. 32A, the nvCPD image produces a discernable image of the defect. However, as can be seen in FIG. 32B, the integrated image of the same differential nvCPD data produces a more distinct image of the defect. FIG. 33 is a graphical representation of the CPD data for each of the trials. In addition, FIG. 34A-B illustrates the precision of the present invention, showing the data for each of the ten measurements in each of the three separate trials.

EXAMPLE 3

In this example, different types of thin metal films were deposited on the same silicon substrate wafer to compare the nvCPD signal with the work function of materials. The wafer was divided into quadrants and each quadrant received unique deposition processing. Four different materials were deposited by DC sputtering on different quadrants of a silicon substrate through a shadow mask. The $1^{st}$ quadrant (top right) was sputtered with copper, the $2^{nd}$ quadrant (clockwise starting with number 1) was coated with chrome, the $3^{rd}$ quadrant with titanium, and the $4^{th}$ with aluminum. The sputtering time was set to achieve a film thickness of 100 angstroms in all quadrants.

Figure 27:
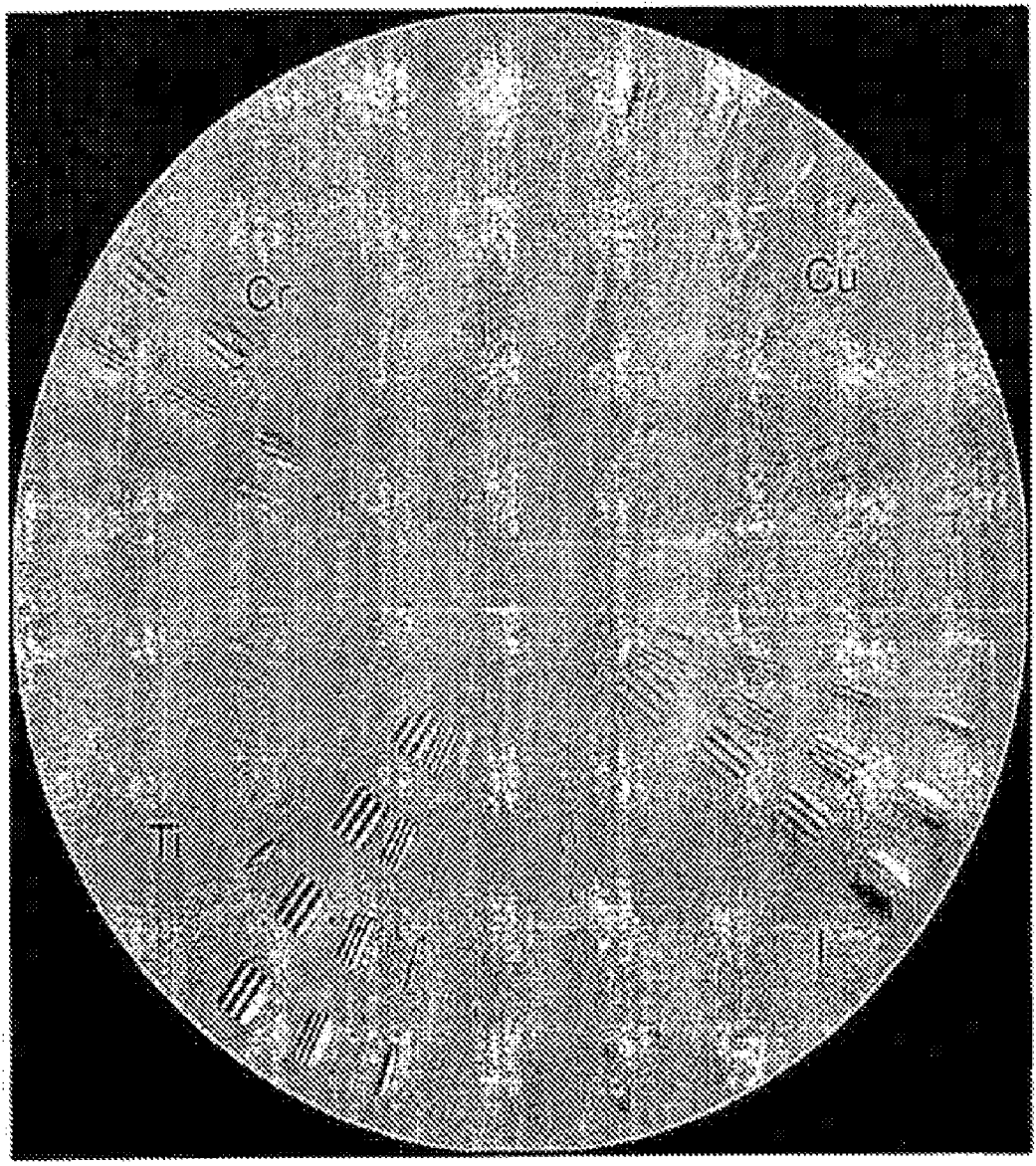
FIG. 27 includes CPD images of four different thin films on a wafer (Cu, Cr, Ti, Al from $1^{st}$ to $4^{th}$ quadrants counterclockwise)
Figure 28:
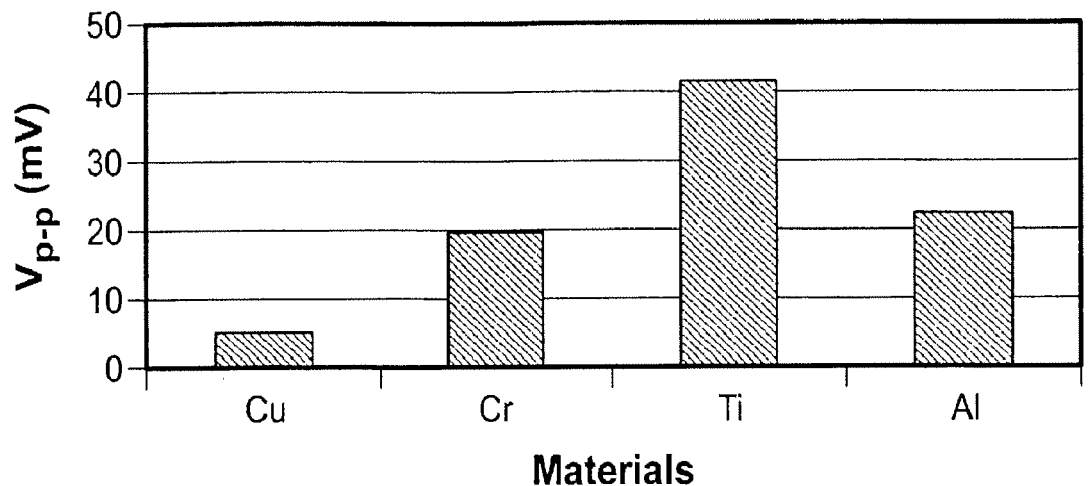
FIG. 28 is a graph of the CPD peak-to-peak intensity vs. materials.

The CPD image of the quadrant wafer is shown in FIG. 27. The lines and dots indicate the area where metal films are deposited. It can be seen that features in four quadrants are all detected by the nvCPD sensor, with different intensity and contrast. The CPD signal intensity can be extracted from a trackwise line plot or straight line plot. In this case, the trackwise line data is used for characterization. FIG. 28 shows the CPD intensity for four materials. It is seen that the peak-to-peak intensity of the CPD signal varies with the material. The copper film generates the lowest peak intensity, and the titanium the highest.

Figure 29:
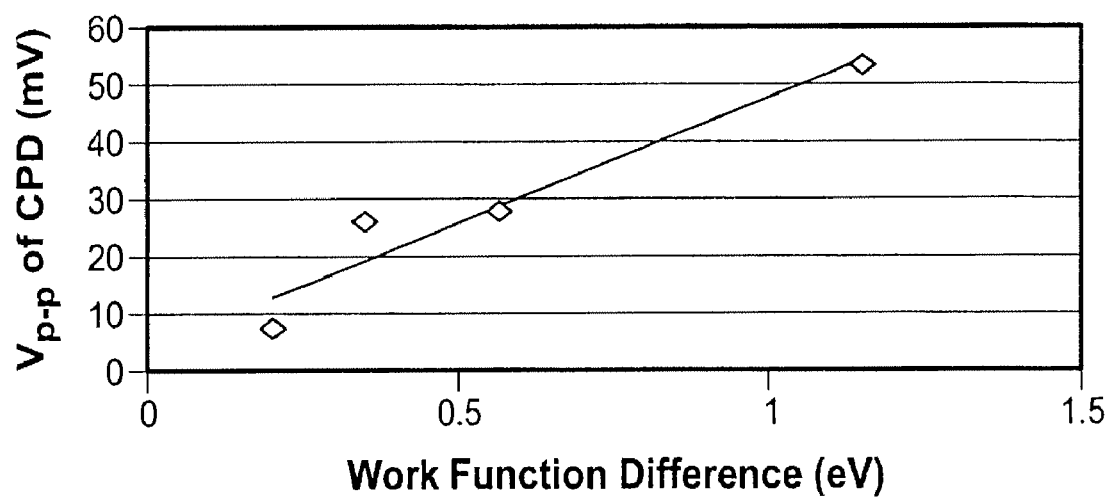
FIG. 29 is a graph of the CPD signal intensity vs. work function difference.

The CPD signal intensity is compared with the work function of materials. Table 3 lists the electronic work function $\Phi$ of materials on the wafer surface. The work function difference ($\Delta\Phi$) between the deposited film and silicon substrate is calculated. It can be found that there is a good correlation between the CPD signal intensity (vCPD) and the work function difference ($\Delta\Phi$). The higher the work function difference, the higher the CPD signal intensity. This can be easily seen from graph in FIG. 29. The CPD signal intensity increases linearly with the work function difference between the deposited film and silicon substrate.

TABLE 3

Work function (Φ) and work function difference (ΔΦ)

| Materials | Φ(eV) | (ΔΦ) (Φfilm − Φsi)(eV) | Vcpd (mV) |
|---|---|---|---|
| Si | 4.85 | | |
| Cu | 4.65 | 0.2 | 7.31 |
| Cr | 4.5 | 0.35 | 25.92 |
| Al | 4.28 | 0.57 | 27.83 |
| Ti | 3.7 | 1.15 | 52.91 |

EXAMPLE 4

In this example, different concentrations of Cu(II) sulfide pentahydrate were applied to a wafer to simulate contamination. Both wafers were scanned with the system of the present invention. The sensitivity of the nvCPD sensor to Cu residue was tested. The Cu contamination was intentionally introduced onto a silicon wafer with a solution containing copper sulfide pentahydrate. First, the solid Cu(II) sulfide pentahydrate was diluted in methanol to different concentrations ranging from $10^{-2}$ mole/liter to $10^{-7}$ mole/liter. Then a drop of each solution was dispensed on each specified spot about 12 mm in diameter on a wafer. A total of 6 copper contaminated spots were made at a radius of 30 mm on the wafer. The wafer was dried naturally from evaporation and then measured with the scanning system.

Figure 30:
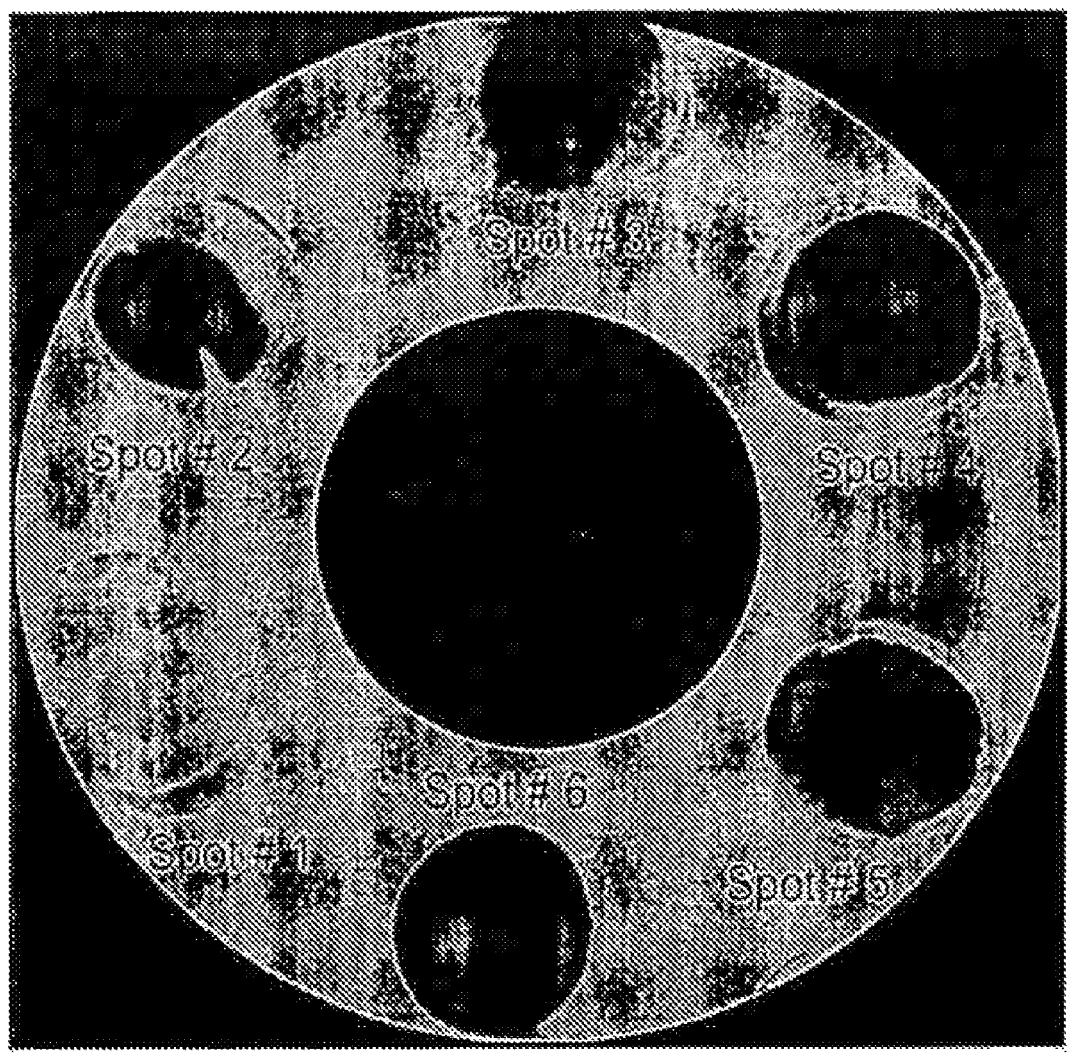
FIG. 30 shows a CPD image of various concentrations of Cu residues on silicon wafer surface.

FIG. 30 shows the work function map taken of a doughnut shape section of the test wafer. As seen in the image, all six contaminated spots are detected. TXRF analysis was subsequently performed on the wafer to measure the atomic concentration of surface Cu at all six spots. The Cu concentration at site 1 was found to be $2.4 \times 10^{11}$ atoms/cm$^2$. The CPD signal intensity at this spot is about 150 mV. This experiment demonstrates that even very low surface concentrations of Cu are detectable by the CPDI technique.

Figure 31:
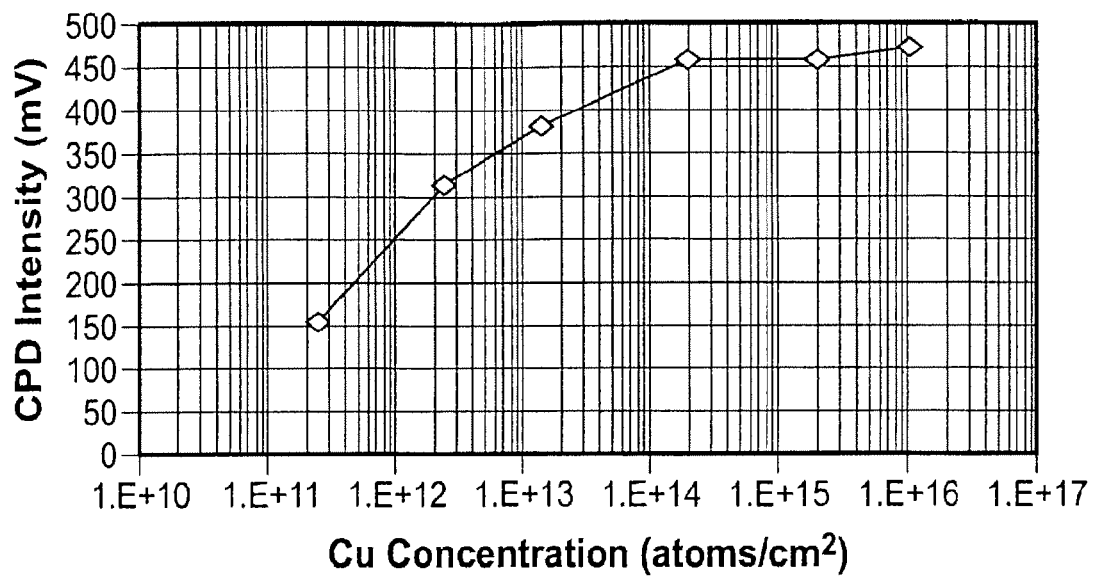
FIG. 31 illustrates the correlation between the nvCPD signal and the concentration of Cu surface contamination on a silicon wafer.

FIG. 31 shows the correlation between the work function variation and Cu surface concentration as measured by TXRF. It can be seen that the signal intensity increases gradually with the increasing Cu concentration at low concentrations then levels off at higher concentrations. This is in agreement with the theoretical prediction. Work function is an inherently surface phenomenon. Once the surface layer is contiguous and unbroken, piling more like atoms on the surface will not affect the work function. For reference, one monolayer of Cu has a surface density of approximately 2E15 atoms/cm2. As the atomic concentration of the contaminant film approaches a contiguous atomic monolayer the addition of more atoms will have diminishing effect.

While preferred embodiments of the invention have been shown and described, it will be clear to those skilled in the art that various changes and modifications can be made without departing from the invention in its broader aspects as set forth in the claims provided hereinafter.

What is claimed is:

1. A system for inspection of a component having a surface with the component undergoing processing to enable providing a commercial product comprising:
    a sample stage for receiving a component;
    a drive system to move the component;
    a contact potential difference sensor system including a non-vibrating contact potential difference probe and a vibrating contact potential difference probe;
    the non-vibrating contact potential difference probe generating a relative contact potential difference signal characteristic of at least one of contaminants and physical defects at the surface of the component as a result of a change in the contact potential difference, the relative contact potential difference signal generated by relative motion of the non-vibrating contact potential difference probe and the component;
    the vibrating contact potential difference probe generating an absolute contact potential difference signal characteristic of at least one of the contaminants and the physical defects at the surface of the component, the absolute contact potential difference signal generated by the vibration of the vibrating contact potential difference probe while positioned over a point on the component; and
    a computer system in communication with the contact potential difference sensor system, the computer system processing the relative contact potential difference signal and the absolute contact potential difference signal to inspect the surface of the component and provide analytical information about at least one of the contaminants and the physical defects of the surface of the component, thereby enabling quality control of the component enabling its use in the commercial product.

2. The system as defined in claim 1 further including an additional surface analysis system to provide supplementary chemical information.

3. The system as defined in claim 2 wherein the additional surface analysis system is selected from the group of TXRF, VPD-ICP-MS, SIMS, automated optical microscopy and laser backscattering.

4. The system as defined in claim 1 wherein the component is selected from the group of a semiconductor wafer and an integrated circuit.

5. The system as defined in claim 1 wherein the system for inspection comprises an in-line system.

6. The system as defined in claim 1 further including an imaging system to display the analytical information.

7. The system as defined in claim 1 further including a positioning assembly in communication with the contact potential difference sensor system, whereby the sensor system can be positioned relative to the component on the sample stage.

8. The system as defined in claim 1 further including a bias voltage system coupled to the component.

9. The system as defined in claim 1 further including a probe height sensor.

10. The system as defined in claim 1 wherein the contact potential difference sensor system comprises a plurality of at least one of the non-vibrating contact potential probe and the vibrating contact potential probe.

11. The system as defined in claim 1 wherein the computer system includes executable software to compare the contact potential difference signals with known chemical patterns to determine chemistry of the contaminants.

12. The system as defined in claim 1 wherein the computer system includes executable software to convert spatial data from the contact potential difference signal into frequency domain data to enable identifying peaks in the frequency domain with particular spatial characteristics.

13. The system as defined in claim 1 wherein the computer system includes executable software to process the non-vibrating contact potential difference signal into wavelet domain signals for removal of noise.

14. The system as defined in claim 1 wherein the computer system includes executable software to carry out an electronic filtering of the contact potential difference signals.

15. The system as defined in claim 1 further including a variable speed mechanical component to decrease velocity of the component in proportion to motion of the non-vibrating contact potential probe, thereby providing the probe with substantially even data exposure.

16. A system for inspection of a semiconductor wafer having a surface with the semiconductor wafer undergoing processing as part of an in-line fabrication system, comprising:
a sample stage for receiving a semiconductor wafer;
a drive system to move the semiconductor wafer;
a contact potential difference sensor system including a non-vibrating contact potential difference probe and a vibrating contact potential difference probe;
the non-vibrating contact potential difference probe generating a relative contact potential difference signal characteristic of at least one of contaminants and physical defects at the surface of the semiconductor wafer and the relative contact potential difference signal generated by relative motion of the non-vibrating contact potential difference probe and the semiconductor wafer;
the vibrating contact potential difference probe generating an absolute contact potential difference signal characteristic of at least one of the contaminants and the physical defects at the surface of the semiconductor wafer, the absolute contact potential difference signal generated by the vibration of the vibrating contact potential difference probe while positioned over a point on the semiconductor wafer; and
a computer system in communication with the contact potential difference sensor system, the computer system processing the relative contact potential difference signal and the absolute contact potential difference signal to inspect the surface of the semiconductor wafer and provide analytical information about at least one of the contaminants and the physical defects of the surface of the semiconductor wafer, thereby enabling quality control of the semiconductor wafer as part of the in-line fabrication system.

17. The system as defined in claim 16 further including a test wafer to establish standards for at least one of the chemical contaminants and the physical defects.

18. The system as defined in claim 16 wherein the semiconductor wafer comprises an integrated circuit.

19. The system as defined in claim 16 further including an imaging system to display the analytical information.

20. The system as defined in claim 16 further including at least one of an additional surface analysis system, a probe height sensor, a bias voltage system and a positioning system.

21. A system for providing quality control information about a component having a surface with the component undergoing processing to provide a commercial product, the system comprising: a sample stage for receiving a component; a contact potential difference sensor system including a non-vibrating contact potential difference probe and a vibrating contact potential difference probe; the non-vibrating contact potential probe generating a first signal characteristic of differences in contact potential difference across the surface of the component, the first signal generated by motion of the non-vibrating contact potential difference probe relative to the component such that the probe moves substantially parallel to the component surface; the vibrating contact potential difference probe generating at least one absolute contact potential difference measurement for at least one point on the surface of the component to provide a measurement signal which results from the change in capacitance generated by the vibration of the vibrating contact potential difference probe, and the first signal from the non- vibrating contact potential probe and the measurement signal from the vibrating probe together providing quality control information about the component; and a computer system in communication with the contact potential difference sensor system. the computer system processing the first signal and the measurement signal to inspect the surface of the component and provide analytical information about at least one of contamination, charging, and physical defects on or near the surface of the component, thereby enabling quality control of the commercial product.

22. The system as defined in claim 21 wherein the component is selected from the group of a semiconductor wafer, a photovoltaic cell, and a flat panel display.

23. The system as defined in claim 21 wherein the vibrating contact potential difference probe and the non-vibrating contact potential probe are the same sensor.

24. The system as defined in claim 21 wherein the contact potential difference sensor system comprises a plurality of at least one of the non-vibrating contact potential difference probe and the vibrating contact potential difference probe.

25. The system as defined in claim 21 wherein the non-vibrating contact potential difference first signal is integrated to produce data representative of relative contact potential difference across the surface of the component.

26. The system as defined in claim 25 wherein the absolute contact potential measurement signal is used to calibrate the integrated non-vibrating contact potential first signal to produce data that is representative of the absolute contact potential difference over an area of the component surface.

27. The system as defined in claim 21 wherein the charging results from electrical charges trapped in an insulating film on the surface of the component.

28. The system as defined in claim 21 wherein the computer system includes executable software to compare the contact potential difference first signal and the measurement signal with known chemical patterns to distinguish between different types of contaminants or defects.

29. The system as defined in claim 21 wherein the relative motion is accomplished by rotating the component about a central axis with the non-vibrating contact potential difference probe positioned at different radii to acquire concentric circular tracks of data.

30. A system for providing quality control information about a component having a surface with the component undergoing processing to provide a commercial product, the system comprising: a sample stage for receiving a component; a contact potential difference sensor system including a non-vibrating contact potential difference probe and a vibrating contact potential difference probe; the non-vibrating contact potential probe generating a first signal characteristic of differences in contact potential difference across the surface of the component, the first signal generated by motion of the non-vibrating contact potential difference probe relative to the component such tat the probe moves substantially parallel to the component surface; the vibrating contact potential difference probe generating one or more absolute contact potential difference measurements at points on the surface of the component to provide a measurement signal which results from the change in capacitance generated by the vibration of the vibrating contact potential difference probe and both the first signal from the non-vibrating contact potential probe and the measurement signal from the vibrating probe together providing quality control information about the component, thereby enabling quality control of the component.

31. the system as defined in claim 30 wherein the non-vibrating contact potential difference first signal is integrated to produce data representative of relative contact potential difference across the surface of the component.

32. The system as defined in claim 30 wherein the charging results from electrical charges trapped in an insulating film on the surface of the component.

33. The system as defined in claim 30 wherein the relative motion is accomplished by rotating the component about a central axis with the non-vibrating contact potential difference probe positioned at different radii to acquire concentric circular tracks of data.

* * * * *